US007951587B2

(12) United States Patent
Römer-Oberdörfer et al.

(10) Patent No.: US 7,951,587 B2
(45) Date of Patent: May 31, 2011

(54) RECOMBINANT MONONEGAVIRAL VIRUS VECTORS

(75) Inventors: Angela Römer-Oberdörfer, Greifswald-Insel Riems (DE); Jutta Veits, Greifswald-Insel Riems (DE); Teshome Mebatsion, Millsboro, DE (US)

(73) Assignee: Intervet International B.V., Boxmeer (NL)

( * ) Notice: Subject to any disclaimer, the term of this patent is extended or adjusted under 35 U.S.C. 154(b) by 218 days.

(21) Appl. No.: 12/293,001

(22) PCT Filed: Mar. 15, 2007

(86) PCT No.: PCT/US2007/064046
§ 371 (c)(1),
(2), (4) Date: Sep. 15, 2008

(87) PCT Pub. No.: WO2007/106882
PCT Pub. Date: Sep. 20, 2007

(65) Prior Publication Data
US 2009/0220539 A1    Sep. 3, 2009

Related U.S. Application Data

(60) Provisional application No. 60/783,194, filed on Mar. 15, 2006.

(30) Foreign Application Priority Data

Mar. 15, 2006 (EP) .................................... 06075628

(51) Int. Cl.
*C12N 1/00* (2006.01)
*A61K 39/145* (2006.01)
*A61K 39/155* (2006.01)
*A61K 39/205* (2006.01)

(52) U.S. Cl. ............... 435/320.1; 424/209.1; 424/211.1; 424/212.1; 424/214.1

(58) Field of Classification Search ........................ None
See application file for complete search history.

(56) References Cited

U.S. PATENT DOCUMENTS

| 6,451,323 B1 * | 9/2002 | Garcia-Sastre et al. ... 424/214.1 |
| 2003/0091590 A1 * | 5/2003 | Pomerantz et al. ........ 424/199.1 |
| 2003/0224017 A1 | 12/2003 | Samal et al. |

FOREIGN PATENT DOCUMENTS

| WO | 9966045 | 12/1999 |
| WO | 0015853 | 3/2000 |
| WO | 0236617 | 5/2002 |
| WO | 2006050984 | 5/2006 |
| WO | 2007104782 | 9/2007 |
| WO | 2007106882 | 9/2007 |

OTHER PUBLICATIONS

Römer-Oberdörfer et al., Journal of General Virology, 1999, 80:2987-2995.*
GenBank accession No. Y18898 (1999) 6 pages.*
Conzelmann et al., Virology, 1990, 175(2):485-488.*
GenBank accession No. M31046 (1990), 5 pages.*
Biachhesi et al., Journal of Virology, 2000, 74(23):11247-11253.*
Morzunov et al., Virus Research, 1995, 38:175-192.*
GenBank accession No. L40883 (1995), 6 pages.*
Bukreyev, A. et al., "Recombinant Newcastle Disease Virus Expressing a Foreign Viral Antigen Is Attenuated and Highly Immunogenic in Primates," Journal of Virology, 79(21):13275-13284 (2005).
Nakaya,

FIG. 1A

Construction of rNDV/AIVH5-A

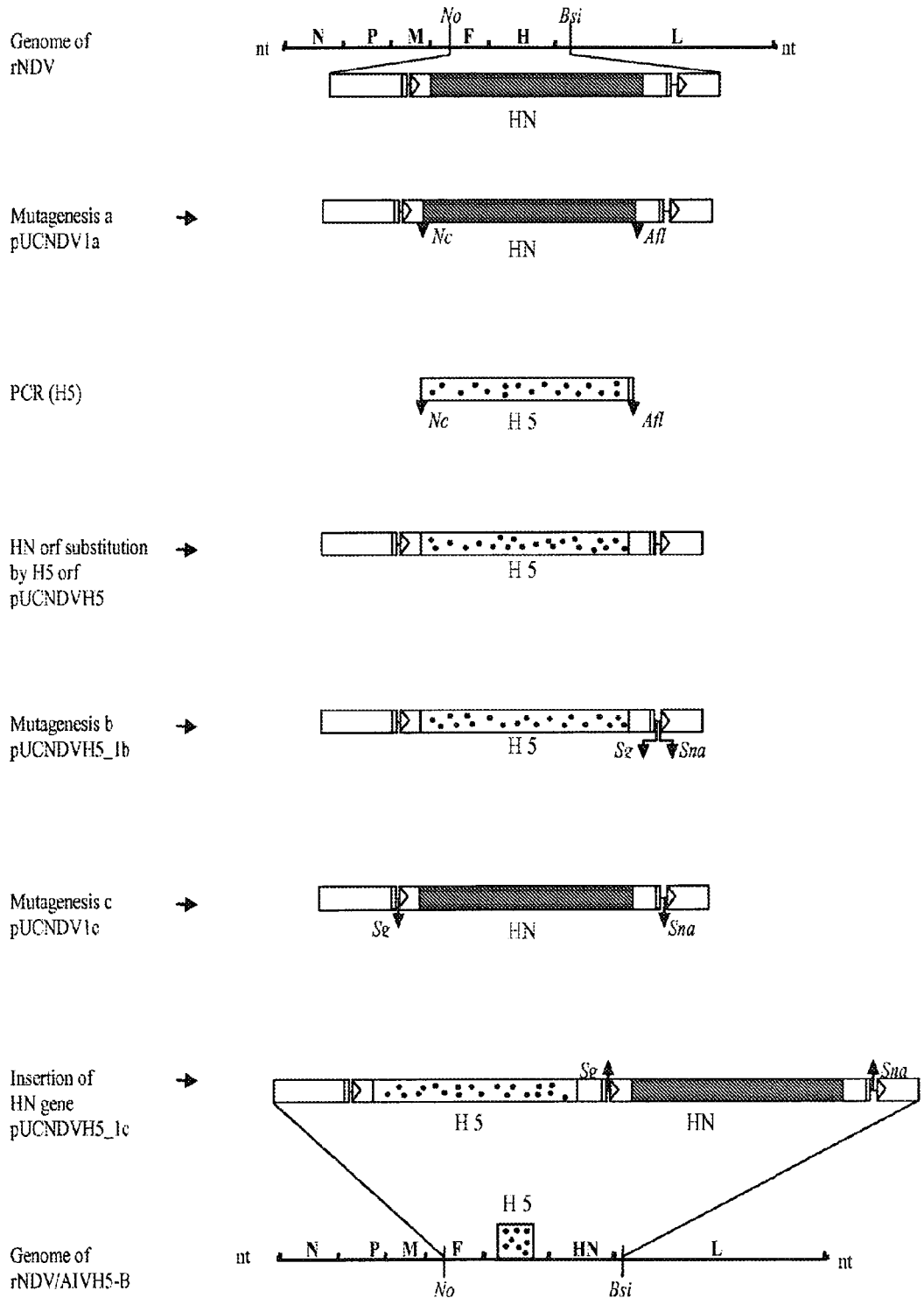

FIG. 2A
NDV Clone 30 HN flanking sequences

| F Gene End | IGR | HN Gene Start | 5'-NCR | ATG – HN Coding Region - TAG | 3'-NCR | HN Gene End |

A, SEQ ID NO: 1        B        C, SEQ ID NO: 2

A
```
         [F-Gene End]         [IGR]            [HN-Gene Start]
   1 TTAAGAAAAA ACTACCGGTT GTAGATGACC AAAGGACGAT ATACGGGTAG
  51 AACGGTAAGA GAGGCCGCCC CTCAATTGCG AGCCAGGCTT CACAACCTCC
 101 GTTCTACCGC TTCACCGACA ACAGTCCTCA ATC
```

[5'-NCR]

B      - ATG - [HN Coding Region] - TAG -

C
```
     [3'-NCR]
   1 TTGAGTCAAT TATAAAGGAG TTGGAAAGAT GGCATTGTAT CACCTATCTT
  51 CTGCGACATC AAGAATCAAA CCGAATGCCG GCGCGTGCTC GAATTCCATG
 101 TTGCCAGTTG ACCACAATCA GCCAGTGCTC ATGCGATCAG ATTAAGCCTT
 151 GTCAATAGTC TCTTGATTAA GAAAAAA
```
                                     [HN-Gene End]

FIG. 2B
rNDV with AIV-H5 gene insert and NDV-HN flanking sequences

| F Gene End | IGR | HN Gene Start | 5'-NCR | ATG – H5 Coding Region - TAG | 3'-NCR | HN Gene End |

A, SEQ ID NO: 3        B        C, SEQ ID NO: 4

```
           [F-Gene End]          [IGR]             [HN-Gene Start]
       1   TTAAGAAAAA ACTACCGGTT GTAGATGACC AAAGGACGAT ATACGGGTAG
A     51   AACGGTAAGA GAGGCCGCCC CTCAATTGCG AGCCAGGCTT CACAACCTCC
     101   GTTCTACCGC TTCACCGACA ACAGTCCTCA ACC
                                    [5'-NCR]
```

B     - ATG - [H5 Coding Region] - TAG -

```
           [3'-NCR]
       1   TTGAGTCAAT TCTAAGGGAG TTGGAAAGAT GGCATTGTAT CACCTATCTT
C     51   CTGCGACATC AAGAATCAAA CCGAATGCCG GCGCGTGCTC GAATTCCATG
     101   TTGCCAGTTG ACCACAATCA GCCAGTGCTC ATGCGATCAG ATTAAGCCTT
     151   GTCAATAGTC TCTTGATTAA GAAAAAA
                           [HN-Gene End]
```

FIG. 3
Northern Blot

Western Blot

FIG. 5
IF test

| | α-AIVH5 | α-NDV |
|---|---|---|
| NDV | | |
| rNDV/AIVH5-A | | |
| rNDV/AIVH5-B | | |
| AIVH | | |
| Neg. | | |

200 μm

FIG. 6
Clinical indices and mortality rates

FIG. 7

Cloning regions of GNCR/SSN constructs

SSNsc Cloning region

```
    BstXI    Ts STOP    IG   Ts START    NheI     HindIII
    CTGG  TGAAAAAAA  CT  AACACCCCT  GCTAGC  A
    CGT TGACC ACTTTTTTT GA TTGTGGGGA CGATCG TTCGA
```

GNCR-b Cloning region

```
    BstXI    Ts STOP    IG    Ts START            5'G-NCR              SnaBI
5'- CTGG  TGAAAAAAA CTATT AACATCCCT CAAAAGACTCAAGGATAC GTACT
3'-CGTTGACC ACTTTTTTT GATAA TTGTAGGGA GTTTTCTGAGTTCCTATG

-SnaBI                         3'G-NCR                            HindIII
5'-          GGCCGT CCTTTCAAGGATCCAAGTCCTGAAGATCACCTCCCCTTGGGGG A
3'- CATGACCGGCA GGAAAGTTGCTAGGTTCAGGACTTCTAGTGGAGGGGAACCCCC TTCGA
```

FIG. 8

Summary of Recombinant Rabies/EIAV Constructs

| Rabies G | EIAV envelope | RV-Env |

| Rabies G | EIAV envelope | RV-EnvG |

FIG. 9
Western blot of Rabies-EIAVenv purified virions:

RECOMBINANT MONONEGAVIRAL VIRUS VECTORS

CROSS REFERENCE TO RELATED APPLICATIONS

This application is the National Phase Entry under 35 U.S.C. §371 of International Application No. PCT/US2007/064046, having an international file date of Mar. 15, 2007; which claims priority to European Application No. EP 06075628.5, filed Mar. 15, 2006 and to U.S. Provisional Application No. 60/783,194, filed Mar. 15, 2006, all of which are hereby incorporated by reference in their entirety.

REFERENCE TO SEQUENCE LISTING

The material saved as "text document" under the file name "SubstituteSequenceListing" created on Mar. 27, 2009 is hereby incorporated by reference.

This invention relates to a recombinant Mononegavirales virus vector harboring an additional transcription unit comprising a foreign gene operatively linked with an upstream Mononegavirales virus gene start (GS) sequence and a downstream Mononegavirales virus gene end (GE) sequence as well as with a vaccine comprising such a recombinant Mononegavirales virus vector.

Live viruses that are able to replicate in an infected host induce a strong and long-lasting immune response against their expressed antigens. They are effective in eliciting both humoral-and cell-mediated immune responses, as well as stimulating cytokine and chemokine pathways. Therefore, live, attenuated viruses offer distinct advantages over vaccine compositions based on either inactivated or subunit immunogens which typically largely only stimulate the humoral arm of the immune system.

Over the last decade recombinant DNA technology has revolutionized the field of genetic engineering of the genomes of both DNA and RNA viruses. In particular, it is now possible to introduce foreign genes into the genome of a virus such that upon replication of the new vector virus in a host animal a foreign protein is expressed that can exert biological effects in the host animal. As such recombinant vector viruses have been exploited not only for the control and prevention of microbial infections, but also for devising target therapies for non-microbial diseases such as malignancies and in gene therapy.

The generation of non-segmented, negative stranded RNA viruses (viruses of the order Mononegavirales) entirely from cloned cDNA by a technique designated as "reverse genetics", first reported in 1994 (Schnell et al., EMBO J., 13, 4195-4203, 1994), has made it possible to use also viruses of the order Mononegavirales (MV) as vectors. Since then studies have been published that describe the use of many viruses of the order MV as viral vectors to express foreign antigens derived from a pathogen aiming at developing vaccines against that pathogen.

The order of Mononegavirales is classified into four main families: Paramyxoviridae, Rhabdoviridae, Filoviridae and Bornaviridae. Viruses belonging to these families have genomes that are represented by a single, negative (−) sense RNA molecule, i.e. the polarity of the RNA genome is opposite to the polarity of messenger RNA (mRNA) that is designated as plus (+) sense. The classification of the main human and veterinary MV viruses is presented in the table below:

TABLE 1

Classification of the viruses within the order of Mononegavirales

| Family | Genus | Species |
| --- | --- | --- |
| Rhabdoviridae | Lyssavirus | Rabies virus (RV) |
|  | Vesiculovirus | Vesicular stomatitis virus (VSV) |
|  | Novirhabdovirus | Infectious hematopoietic necrosis virus (IHNV) |
| Paramyxoviridae | Respirovirus | Sendai virus (SeV) |
|  |  | Human parainfluenza virus type 1 and type 3 (hPIV 1/3) |
|  |  | Bovine parainfluenza virus type 3 (bPIV 3) |
|  | Morbillivirus | Measles virus (MV) |
|  |  | Rinderpest virus |
|  |  | Canine distemper virus (CDV) |
|  | Rubulavirus | Simian virus 5 (SV-5) |
|  |  | Human parainfluenza virus type 2 (hPIV 2) |
|  |  | Mumps virus |
|  | Avulavirus | Newcastle disease virus (NDV) |
|  | Pneumovirus | Human respiratory syncytial virus (hRSV) |
|  |  | Bovine respiratory syncytial virus (bRSV) |
| Filoviridae | Ebola-like virus | Ebolavirus |
|  |  | Marburg virus |

The genomic organization and details of the life cycle of viruses of the order MV is well understood these days and is reviewed by various authors (Neumann et al., J. Gen. Virology 83, 2635-2662, 2002; Whelan et al., Curr. Top. Microbiol. Immunol. 203, 63-119, 2004; Conzelmann, K.; Curr. Top. Microbiol. Immunol. 203, 141, 2004). Although Mononegavirales viruses have different hosts and distinct morphological and biological properties, they have many features in common, such as genomic organization and the elements essential for their typical mode of replication and gene expression, illustrating that they have originated from a common ancestor. They are enveloped viruses that replicate in the cytoplasma of the cell and produce mRNAs that are not spliced.

A Mononegavirales virus consists of two major functional units, a ribonucleoprotein (RNP) complex and an envelope. The complete genome sequences for representative viruses of the genera of all the families mentioned above have been determined. The genomes range in size from about 9.000 nucleotides to about 19.000 and they contain from 5 to 10 genes. The structure and the organization of the genomes of the MV viruses are very similar and are governed by their particular mode of gene expression. All of the MV virus genomes comprise three core genes encoding: a nucleoprotein (N or NP), a phosphoprotein (P) and a RNA-dependent RNA polymerase (L). The viral envelope is composed of a matrix (M) protein and one or more transmembrane glycoproteins (e.g. G, HN and F proteins) that play a role in virus assembly/budding as well as in the cell attachment and/or entry of the virus. Depending on the genus, the protein repertoire is extended by accessory proteins that display certain specific regulatory functions in transcription and virus replication or that are involved in virus host reactions (e.g. C, V and NS proteins). The gene order of MV viruses is highly conserved with the core genes N and P, at or near the 3' terminus and with the large (L) gene at the 5' distal position. The M, the surface glycoprotein genes, as well as the other accessory genes, are located between the N. P and L genes.

In the RNP complex, the genomic or antigenomic RNA is tightly encapsidated with the N protein and is associated with the RNA-dependent RNA polymerase that consists of the L and P protein. After infection of a cell, the RNP complex, but not the naked RNA genome, serves as a template for two distinct RNA synthesis functions, i.e. transcription of subgenomic mRNAs and replication of full length genomic RNA.

All of the tandemly arranged genes are separated by so called "gene junction" structures. A gene junction comprises a conserved "gene end" (GE) sequence, a non-transcribed "intergenic region" (IGR) and a conserved "gene start" (GS) sequence. These sequences are both sufficient and necessary for gene transcription. During transcription each gene is sequentially transcribed into mRNA by the viral RNA-dependent RNA polymerase that starts the transcription process at the 3' end of the genomic RNA at the first GS sequence. At each gene junction transcription is interrupted as a result of the disengagement of the RNA polymerase at the GE sequence. Re-initiation of transcription occurs at the subsequent GS sequence, although with a reduced efficiency. As a result of this interrupted process, also designated as a "stop-start" process, attenuation of transcription occurs at each gene junction as a result of which the 3' proximal genes on a MV virus genome are transcribed more abundantly than successive down stream genes. The modular form of transcription of MV virus genes in which each gene is part of a separate cistron or transcription unit makes these viruses extremely suited for the insertion and expression of foreign genes. Each transcription unit in a MV virus genome comprises the following elements: 3'—GS-open reading frame (ORF)GE—5'.

At the 3'-and 5'-genomic termini all of the MV virus genomes have a short non-transcribed region called "leader" (about 40-50 nt) and "trailer" (about 20-600 nt), respectively. The leader and trailer sequences are essential sequences that control the replication of genomic RNA, viral encapsidation and -packaging.

The reverse genetics technology and the rescue of infectious MV virus have made it possible to manipulate its RNA genome through its cDNA copy. The minimal replication initiation complex required to synthesize viral RNA is the RNP complex. Infectious MV virus can be rescued by intracellular co-expression of (anti)genomic RNAs and the appropriate support proteins from (T7) RNA polymerase driven plasmids. Since the initial report in 1994 by Schnell et al., 1994 (supra), reliable recovery of many MV virus species has been achieved based on the original protocol (or slight variations thereof).

Newcastle disease and avian influenza are important diseases of poultry, which can cause severe economic losses in the poultry industry worldwide. Newcastle disease virus is a non-segmented, negative stranded RNA virus within the order of MV. The genome, which is about 15 kb in length, contains six genes which encode the nucleoprotein (NP), phosphoprotein and V protein (PV), matrix (M) protein, fusion (F) protein, hemagglutinin-neuraminidase (HN) protein and RNA-dependent RNA polymerase or large (L) protein. The NDV genes are arranged sequentially in the order 3'-NP-P-M-F-HN-L-5', and are separated by intergenic regions of different length. All genes are preceded by a gene start (GS) sequence which is followed by a noncoding region, the open reading frame encoding the NDV proteins, a second noncoding region and the gene end (GE) sequence. The length of the NDV genome is a multiple of six, which has to be considered for the introduction of foreign genes.

Avian influenza (AI) is a disease of poultry characterized by mild respiratory signs to severe disease with high mortality. The causative agent is an avian influenza A virus (AIV) belonging to the family Orthomyxoviridae. AIV contains eight genomic RNA segments of negative polarity which encode 10 proteins. Based on the antigenicity of the surface glycoproteins hemagglutinin (HA) and neuraminidase (N), AI viruses were subtyped. Up to now, 16 hemagglutinin (H1-H16) and nine neuraminidase (N1-N9) subtypes are known. Antibodies to H and N are important in humoral immune response and inhibit infection or prevent disease.

Avian influenza and Newcastle disease viruses can be grouped into two distinct pathotypes according to their virulence. Symptoms caused by low pathogenic AIV (LPAI) or lentogenic NDV are considered of less relevance. In contrast, highly pathogenic avian influenza (HPAI) and Newcastle disease caused by high virulent viruses (NDV: mesogenic and velogenic strains) are notifiable diseases.

Whereas routine vaccination against NDV with lentogenic NDV strains is performed to protect chicken against highly virulent NDV strains, vaccination against HPAI is not performed in most countries, since HPAI is controlled by an eradication strategy. However, vaccination may be used as a strategy to minimize losses and to reduce the incidence of disease. Immunity induced by vaccines is subtype specific, which means that a subtype H5 vaccine can protect against H5 AIV but not against the other H subtypes. Normally, influenza virus replication is restricted to the lungs because hemagglutinin of LPAI viruses can be cleaved only by tryptase Clara, a serine protease restricted to the lungs. So far, all HPAI viruses have been of H5 and H7 subtype. These HPAI viruses contain multiple basic amino acids at the H cleavage site so that it can be cleaved by ubiquitous furin and subtilisin-like enzymes into the subunits HA1 and HA2. Such viruses can therefore grow in other organs.

Subtype H5 and H7 vaccines can provide protection of chickens and turkeys against clinical signs and death following infection with HPAI. In addition to conventional inactivated oil-based whole AIV, vector virus, subunit protein and DNA vaccines have been shown experimentally to be effective for immunization against AI. Since the advent of reverse genetics for different viruses the generation of recombinant viruses for use as vaccine vectors is an important application. Different recombinant negative-strand RNA viruses expressing foreign proteins have been constructed. Also, the hemagglutinin of AIV was inserted into different vector viruses like the infectious laryngotracheitis virus (ILTV) (Luschow et al., Vaccine 19, 4249-59, 2001), Rinderpest virus (Walsh et al., J. Virol. 74, 10165-75, 2000) and vesicular stomatitis virus (VSV) (Roberts et al., J. Virol 247, 4704-11, 1998).

Rinderpestvirus was also used as vector virus for the expression of the foot-and mouth-disease virus VP1 capsid protein (Baron et al., 1999, J. of Gen. Virol., vol. 80, p. 2031-2039).

Tao et al. (1998, J. of Virol., vol. 72, p. 29552961) describe the construction of a chimeric human parainfluenza virus (hPIV) type 3, wherein the HN and F genes from hPIV type 1 were used for a replacement of (not an addition to) the endogenous hPIV type 3 HN and F genes.

Also NDV was used for the expression of AIV hemagglutinin. The hemagglutinin gene of influenza A/WSN/33 was inserted between P and M genes of NDV strain Hitchner B1. This recombinant protected mice against lethal infection although there was a detectable weight loss in mice which recovered fully within 10 days Nakaya et al. (J. Virol. 75, 11868-73, 2001). A further recombinant NOV with the same insertion site for the foreign gene expressed the H7 of a LPAI but only 40% of the vaccinated chicken were protected from both velogenic NDV and HPAI (Swayne et al., Avian Dis. 47 1047-50, 2003).

These publications however do not disclose any advantageous effect of the so-called non-coding regions of endogenous MV genes on the expression of additional foreign genes inserted into the genome of an MV vector.

SUMMARY OF THE INVENTION

It is an object of this invention to provide a recombinant MV virus vector that displays a higher expression level of a protein encoded by a foreign gene inserted into the genome of the vector virus and/or that shows a stronger immunogenicity than existing MV virus vectors.

The present inventors have found that this object can be met by a recombinant Mononegavirales virus vector according to the invention. Therefore, the present invention provides a recombinant Mononegavirales virus vector harboring an additional transcription unit comprising a foreign gene operatively linked with an upstream Mononegavirales virus gene start (GS) sequence and a downstream Mononegavirales virus gene end (GE) sequence, characterized in that between the GS sequence and a start codon of the foreign gene and between a stop codon of the foreign gene and the GE sequence, a 3' non-coding region-and a 5' non-coding region (genome sense) of a Mononegavirales virus gene are located, respectively.

It is noted that the indications of the polarity of the nucleic acid strands here and in the rest of the text are given in the genome (–) sense, except in the context of mRNA and cDNA sequences.

BRIEF DESCRIPTION OF THE FIGURES

FIG. 1A: The construction of cDNA encoding NDV antigenomic RNA containing the AIV H5 gene by insertion of the H5 ORF between the F and HN genes of NDV.

FIG. 1B: The construction of a full length plasmid containing the AIV H5 gene for generation of rNDV/AIVH5-B.

FIG. 2A: Nucleotide sequences of regions flanking the H5 ORF in a NDV vector, A (SEQ ID NO.:1) and C (SEQ ID NO.:2).

FIG. 2B: Nucleotide sequences of regions flanking the H5 ORF in the NDV vector, A (SEQ ID NO.: 3) and C (SEQ ID NO.:4).

FIG. 3: Northern Blot analysis to verify transcription of initial AIV H5 genes in rNDV/AIVH5-A and -B using total RNA of NDV/AIVH5 recombinant infected primary chicken embryo fibroblasts.

FIG. 5: Immunoflorescence test showing H5 expression in infected CEF cells.

FIG. 6: Comparison of clinical index and mortality for chickens immunized with rNDV/AIVH5-A and rNDV/AIVH5-B against non-immunized controls after challenge with highly pathogenic AIV.

FIG. 7: Construct GNCR-b containing non-coding regions and minimum transcription unit. SSNsc cloning region SEQ ID NO.: 20 and SEQ ID NO.: 21 (reverse). GNCR-b SEQ ID NO.: 22, SEQ ID NO.:23 (reverse), SEQ ID NO.: 24 and SEQ ID NO.: 25 (reverse).

FIG. 8: Recombinant rabies viruses RV-env and RV-envG.

FIG. 9: Western Blot of Rabies EIAV env purified viron.

DETAILED DESCRIPTION OF THE INVENTION

Figure 3:
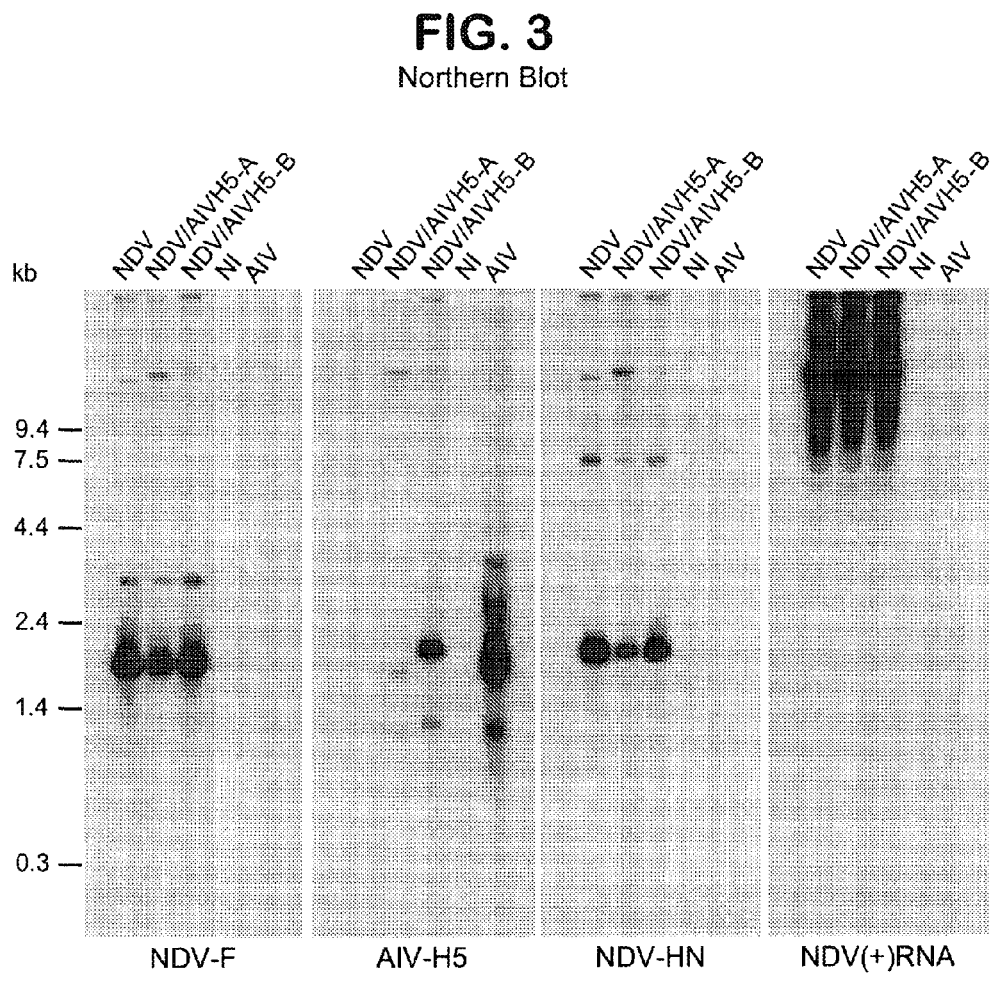
Figure 4:
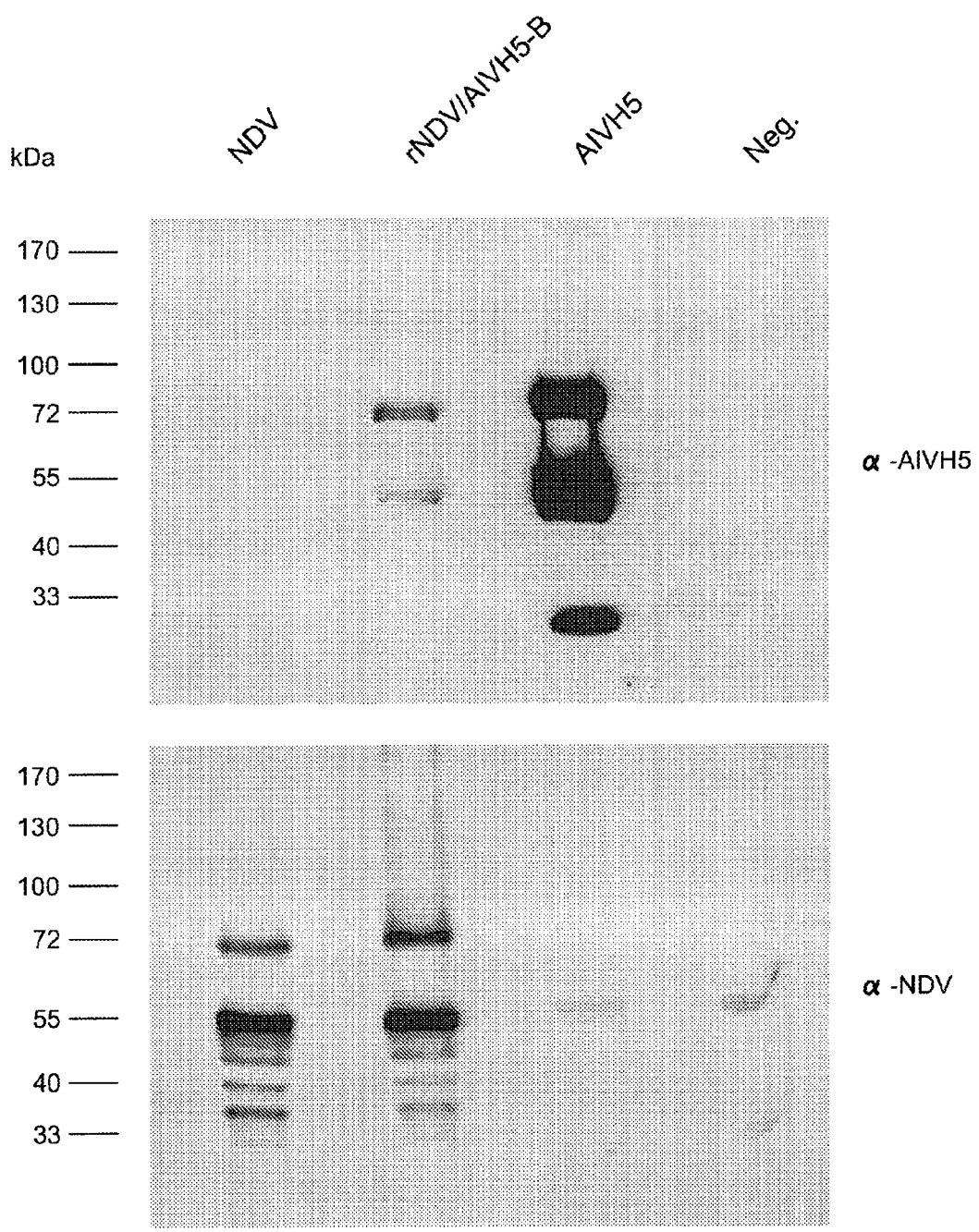
FIG. 4: Western Blot analysis showing the H5 protein to be detectable in only rNDV/AIVH5-B infected cells.

It has been found that the presence of the 3'-and 5' non-coding regions of a MV virus gene in a transcription unit comprising a foreign gene inserted into the genome of a MV virus has a positive effect on the transcription and/or expression of the foreign gene. It is shown in FIG. 3 that engineering the non-coding regions of a MV virus gene between a GS sequence and an avian influenza virus (AIV) hemagglutinin (HA) gene and between the AIV HA gene and a GE sequence increases the amount of HA mRNA synthesized by a MV virus vector harboring that AIV HA gene. A positive effect is also observed on the protein expression level: comparison of the MV virus vectors only showed an intense immunological staining with AIV HA-specific antiserum in case the MV virus vector harboring the foreign AIV HA gene was flanked by the non-coding regions (FIG. 4). Therefore, it has been found that, although the inventors do not want to be bound to any theory or model that might explain these observations, the presence of MV virus non-coding regions flanking a foreign gene, has a positive effect on the performance of the resulting MV virus vector.

A foreign gene is a polynucleotide molecule that encodes a polypeptide or protein and that is not present in nature in the genome of the recipient MV virus.

As already outlined in detail above, a common characteristic of the genomic organization of MV viruses is their modular form of transcription wherein tandemly arranged transcription units are successively transcribed. In a wild-type MV virus the transcribed genes are flanked (i) at their 3' end with a GS sequence and a nucleotide sequence designated in the art as "non-coding region", and (ii) at their 5' end with a nucleotide sequence also designated as "non-coding region" and a GE sequence. Therefore, the term (3' or 5') "non-coding region" as used herein defines a nucleotide sequence that is located upstream (3') or downstream (5') of a natural gene of a MV virus and that spans the region between the GS sequence and the start codon (ATG) of the MV virus gene and the region between the stop codon (TAA, TAG or TGA) of the MV virus gene and the GE sequence, respectively. The non-coding regions used herein are derived from a gene of the same virus as the vector virus (i.e. the non-coding regions are homologous to the MV virus vector).

Detailed information of the genomic organization of MV viruses is known in the art, including the nucleotide sequences of the various MV virus genes and their transcription control (GS and GE) sequences and non-coding sequences that flank the genes. Such information is, for example, available from the database of the National Center for Biotechnology Informationv (NCBI), e.g. via their webpage on the internet; see Tables 2 and 3).

The non-coding sequences that are preferably used in this invention are derived from natural MV virus genes, but substitution of one or more nucleotides in a natural non-coding region is also considered to be within the invention. In particular, nucleotide substitutions are contemplated that are located immediately up-or downstream of the start/stop codon of the foreign gene, respectively, and result from the introduction of artificial restriction enzyme cleavage sites that allow the genetic manipulation of these regions.

In a preferred recombinant MV virus vector according to the present invention the non-coding regions are of a gene encoding a MV virus envelope protein, in particular a M, G, F or HN protein, or a RNP protein, in particular, a N, P or L protein.

In a particularly preferred recombinant MV virus according to the invention the non-coding regions are of a gene encoding a F or HN protein.

Specific nucleotide sequences of non-coding regions to be used in a recombinant MV virus vector according to the inventions are presented in the Table 3.

TABLE 2

Genome- and vector information on Mononegavirales viruses

| MV virus | Genome information: NCBI accession no. | Recombinant virus vector reference |
|---|---|---|
| RV | NC_001542 | Mebatsion et al., PNAS 93, 7310-14, 1996 |
| VSV | NC_001560 | Kretzschmar et al., J. Virol. 71, 5982-89, 1997 |
| IHNV | NC_001652 | — |
| SeV | NC_001552 | Sakai et al., FEBS Lett. 456, 221-6, 1999 |
| hPIV 1 | NC_003461 | — |
| H PIV 3 | NC_001796 | Tao et al., J. Virol. 74, 6448-58, 2000 |
| bPIV 3 | NC_002161 | Tang et al., Vaccine 23, 1657-67, 2005 |
| Measles virus | NC_001498 | Singh et al., J. Virol. 73, 4823-28, 1999 |
| Rinderpest virus | NC_006296 | Walsh et al., J. Gen. Virol. 81, 709-18, 2000 |
| CDV | NC_001921 | Plattet et al., Virus Res. 101, 147-53, 2004 |
| SV 50 | NC_006430 | He et al., Virology 237, 249-60, 1997 |
| NDV | NC_002617 | Zhao et al., J. Gen. Virol. 84, 781-88, 2003 |
| Mumps virus | NC_002200 | — |
| hPIV 2 | NC_003443 | — |
| hRSV | NC_001781 | Bukreyev et al., PNAS 96, 2367-72, 1999 |
| bRSV | NC_001989 | Stope et al., J. Virol., 75, 9367-77, 2001 |
| Ebola virus | NC_006432 | — |
| Marburg virus | NC_001608 | — |

The GS and GE sequences to be used in this invention as the transcriptional control sequences are preferably those derived from the natural genes of the MV viruses. It is believed that these sequences modulate the activity of the RNA polymerase during the transcription process, in particular in the process of transcription initiation and mRNA 5' end modification and in control of transcription 3' end polyadenylation and termination. For each MV virus, the beginning of each gene is marked by a sequence of about 10 nucleotides. Whereas in some MV virus species the GS sequences are the same for each gene, the GS sequences in the genome of other MV virus species may display subtle differences.

In view of their common function in mRNA 3' end poly-A tail formation and transcription termination, the GE sequences in MV viruses share common sequence features. A typical GE sequence comprises a U-tract of between 4-8 nucleotides in length. Furthermore, there is a strong conservation of a C-residue directly upstream of the U-tract and which is preceded by a stretch of nucleotides that is A/U rich. In various GE sequences the 4 nucleotides directly upstream of the U-tract is composed of 3'-AUUC-5'.

The transcriptional control sequences that define the gene borders or gene junctions of MV virus genes have been identified for many MV virus genes by comparing the nucleotide sequences in the genomic template and the nucleotide sequences present at the mRNA termini. In addition many studies have identified GS and GE consensus sequences that are required for efficient gene expression. General features and specific examples of GS and GE sequences can be derived from the information in the NCBI sequence database (see Table 2 for NCBI accession no. 's) and are also reviewed by Neumann et al.(J. Virol. 83, 2635-2662, 2002), and Whelan et al., (Current Topics Microbiol. Immunol. 203, 63-119, 2004).

Specifically preferred GS and GE sequences to be used in a recombinant MV virus vector according to the invention are listed in Table 3, although it is recognized that a precise border between GS-, NCR-and GE sequences can not always be determined. This sequence information is disclosed in the NCBI database (see accession no. in Table 2). For NDV, reference is made to EMBL accession no. Y18898, for RV to GenBank accession no. M31046.

TABLE 3

Gene junction sequence information of various MV genes (+ sense)

| Virus | GS (SEQ ID NO) | NCR (nt) between GS and start codon | ORF | NCR (nt) between stop codon and GE | GE (SEQ ID NO) | IGR (between GE and GS) (SEQ ID NO) |
|---|---|---|---|---|---|---|
| RV | aacacccct | 3 | N | 50 | tgaaaaaaa | ct |
|  | aacacccct | 20 | P | 59 | tgaaaaaaa | caggc |
|  | aacaccact | 6 | M | 171 | tgaaaaaaa | ctatt |
|  | aacatccct | 18 | G | 459 | agaaaaaaa | cattagatcagaag aacaactggc |
|  | aacacttct | 21 | L | 52 | tgaaaaaaa |  |
| IHNV | ggcacttcagttg (29) | 100 | NP | 70 | tagaaaaaaa (30) | t |
|  | ggcactatagtgc (31) | 25 | P | 32 | agaaaaaaa | t |
|  | ggcacgcaagtgt (32) | 41 | M2 | 90 | agacagaaaaaaa (33) | t |
|  | ggcacttttgtgc (34) | 39 | G | 28 | agacagaaaaaaa (33) | c |
|  | ggcacatttgtgc (35) | 14 | NV | −6 | _agatag_aaaaaaa (36) | t |
|  | ggcacttttgtgc (34) | 64 | L | 41 | agatacaaaaaaa (37) |  |
| Sendai virus | agggtcaaag (38) | 54 | NP | 34 | taagaaaaa | ctt |
|  | agggtgaaag (39) | 93 | P | 74 | taagaaaaa | ctt |
|  | agggtgaaag (39) | 22 | M | 85 | taagaaaaa | ctt |
|  | agggataaag | 43 | F | 61 | taagaaaaa | ctt |

TABLE 3-continued

Gene junction sequence information of various MV genes (+ sense)

| Virus | GS (SEQ ID NO) | NCR (nt) between GS and start codon | ORF | NCR (nt) between stop codon and GE | GE (SEQ ID NO) | IGR (between GE and GS) (SEQ ID NO) |
|---|---|---|---|---|---|---|
| | (40) | | | | | |
| | agggtgaaag (39) | 46 | HN | 95 | taagaaaaa | ccc |
| | agggtgaatg (41) | 18 | L | 76 | taagaaaaa | |
| hPIV1 | agggtaaag | 54 | N | 31 | aagtaagaaaaa (42) | ctt |
| | agggtgaatg (43) | 93 | P | 71 | aattaagaaaaa (44) | ctt |
| | agggtcaaag (38) | 22 | M | 82 | aaataagaaaaa (45) | cgt |
| | agggacaaag (46) | 265 | F | 76 | aagtaagaaaaa (42) | ctt |
| | agggttaaag (47) | 46 | HN | 98 | gaataagaaaaa (48) | ctt |
| | agggttaatg (49) | 18 | L | 88 | tagtaagaaaaa (50) | |
| bPIV3 | aggattaaag (51) | 45 | N | 34 | taagaaaaa | ctt |
| | aggattaatg (49) | 69 | P | 116 | taagaaaaa | ctt |
| | aggatgaaag (52) | 22 | M | 51 | aaacaaaaa | ctt |
| | aggatcaaag (53) | 101 | F | 26 | tacaaaaaa | ctt |
| | aggaacaaag (54) | 63 | HN | 86 | taataaaaaa (55) | ctt |
| | aggagaaaag (56) | 12 | L | 62 | taagaaaaa | |
| hPIV3 | aggattaaag (51) | 45 | NP | 34 | taagaaaaa | ctt |
| | aggattaag | 69 | P | 53 | taagaaaaa | ctt |
| | aggattaaag (51) | 22 | M | 51 | taatcaaaaa (57) | ctt |
| | aggacaaaag (58) | 183 | F | 28 | ttataaaaaa (59) | ctt |
| | aggagtaaag (60) | 63 | HN | 81 | tataaaaaa | ctt |
| | aggagcaaag (61) | 12 | L | 62 | taataaaaa | |
| Measles virus | aggattcaaag (62) | 42 | N | 49 | ttataaaaaa (59) | ctt |
| | aggaaccagg (63) | 50 | P | 62 | ttataaaaaa (59) | ctt |
| | aggagcaaag (61) | 22 | M | 417 | taaacaaaaa | ctt |
| | agggccaagg (64) | 574 | F | 128 | taattaaaa | ctt |
| | agggtgcaag (65) | 10 | H | 74 | ttaagaaaaa (66) | cgt |
| | agggtccaag (67) | 12 | L | 59 | ttaagaaaaa (68) | |
| Rinder-pest virus | aggattcaag (69) | 42 | N | 49 | ttataaaaaa (59) | ctt |
| | aggacccagg (70) | 49 | P | 62 | ttataaaaaa (59) | ctt |
| | aggagcaaag (71) | 22 | M | 408 | taccaaacaaaa (72) | ctt |
| | agggtcaaag (39) | 579 | F | 125 | tataaacaaaaa (73) | ctt |
| | aggatgcaag (74) | 10 | H | 98 | ttataaaaaa (59) | cgt |
| | agggtccaag (67) | 12 | L | 60 | taagaaaaa | |

TABLE 3-continued

Gene junction sequence information of various MV genes (+ sense)

| Virus | GS (SEQ ID NO) | NCR (nt) between GS and start codon | ORF | NCR (nt) between stop codon and GE | GE (SEQ ID NO) | IGR (between GE and GS) (SEQ ID NO) |
|---|---|---|---|---|---|---|
| CDV | agggtcaatg (75) | 42 | N | 49 | ttataaaaaa (59) | ctt |
|  | aggacccagg (76) | 49 | P | 62 | ttataaaaaa (59) | ctt |
|  | aggacacaag (77) | 22 | M | 394 | taattaatcaaaa (78) | ctt |
|  | agggtccagg (79) | 16 | F | 122 | ttaaagaaaa (80) | ctt |
|  | agggctcagg (81) | 10 | H | 100 | ttataaaaaa (82) | cta |
|  | aggatccaag (83) | 12 | L | 53 | tacgaaaaaaaa (84) |  |
| SV5 | aggtccggaacct (85) | 83 | NP | 92 | tttaaagaaaaaaa (86) | t |
|  | aggcccggacgggt (87) | 47 | P | 54 | ttttagaaaaaa (88) | cgattaacgataaa ta (89) |
|  | agcccgaacact (90) | 20 | M | 193 | ttcaaagaaaa (91) | caatcatattaaga ctatccta (92) |
|  | agcacgaacccat (93) | 15 | F | 25 | tttttaagaaaaaaa (94) | cgat |
|  | aggaccgaacct (95) | 67 | SH | 64 | ttttaaagaaaaaa (96) | ta |
|  | aggcccgaacact (97) | 54 | HN | 99 | ttttaagaaaaa (98) | ccaaagagaacaat (99) |
|  | aggccaga*atg* (100) | −3 | L | 22 | Tttaagaaaaaa (101) |  |
| VSV | aacagtaatc (102) | 3 | NP | 42 | tgaaaaaaa | ct |
|  | aacagatatc (103) | 0 | NS | −3 | *tga*aaaaaa | gt |
|  | aacagatatc (103) | 31 | M | 98 | tgaaaaaaa | ct |
|  | aacagagatc (104) | 19 | G | 98 | tgaaaaaaa | ct |
|  | aacagcaatc (105) | 0 | L | 31 | tgaaaaaaa |  |
| NDV | acgggtagaa (106) | 56 | NP | 200 | ttagaaaaaa (107) | gt |
|  | acgggtagaa (106) | 73 | P | 169 | ttaagaaaaaa (108) | t |
|  | acgggtagaa (106) | 24 | M | 102 | ttagaaaaaa (107) | c |
|  | acgggtagaa (106) | 36 | F | 73 | ttaagaaaaa (66) | ctaccggttgtagat gaccaaaggacgata t (109) |
|  | acgggtagaa (106) | 81 | HN | 166 | ttaagaaaaaa (108) | tgtaagtggcaatga gatacaaggcaaaac agctcatggtaaata at (110) |
|  | acgggtagga (111) | 1 | L | 67 | ttagaaaaaa (107) |  |

In a preferred recombinant MV virus vector of the invention the GS-, GE sequence and non-coding regions are derived from the same MV virus gene.

Methods for the preparation of a recombinant MV virus vector harboring an additional transcription unit comprising a foreign gene are well known in the art. For example, Table 2 refers to documents that describe the preparation of such recombinant vector viruses for various MV virus species. In principle, the method used in the present invention is the same as that in the prior art, except that the foreign gene to be inserted into the MV virus genome is flanked by the appropriate 3'-and 5'-non-coding regions, as defined above.

In a general method according to the invention the recombinant MV virus vector is prepared by inserting an isolated nucleic acid molecule comprising (i) a foreign gene flanked by the 3'-and 5'-non-coding regions as defined above and (ii) the appropriate transcriptional control sequences, into the genome of the MV virus, such that in the resulting MV virus vector the foreign gene is both preceded and followed by a MV virus gene junction, in particular by a genomic nucleotide sequence fragment comprising GE-IGR-GS elements.

The presence of such upstream and downstream elements guarantee the appropriate transcription not only of the inserted foreign genes, but also of the homologous MV virus genes that are located up-and downstream of the inserted foreign gene.

More in particular, in this method the isolated nucleic acid molecule and the genome of the MV virus are used in their cDNA form (+sense). This allows easy manipulation and insertion of the desired nucleic acid molecules into the viral genome.

In general, various parts of the genome could be used for the insertion of the foreign gene, between two genes, i.e. in intergenic regions (IGR), 3' or 5' non-coding regions of a gene as well as 3' promoter-proximal (before the N/NP genes) or 5' distal end (after the L genes) of a genome.

The foreign gene could advantageously be inserted before the N/NP gene, between NP-P, P-M, M-G/F, G/F-HN, HN-L and after L gene.

The simplest way is to use an already existing restriction enzyme (RE) recognition sequence at one of these sites by cutting with the enzyme and introducing an appropriate transcription cassette. Since naturally existing restriction enzyme recognition sequences are not always located at the desired location, RE recognition sites could be introduced into the genome conventionally by site directed-or PCR mutagenesis. Examples of suitable IGRs for insertion of the foreign gene can be found in Table 3.

The composition of the transcription cassette to be inserted depends on the site of insertion. For example, in case a transcription cassette is inserted into an IGR the cassette may comprise the following elements: 3' RE recognition site-GS-non coding region-ORF (of foreign gene)-non coding region-GE-RE recognition site 5'.

Alternatively, in case a transcription cassette is introduced into a 5' non-coding region of a natural MV virus gene the cassette may be composed of: 3' RE recognition site-GE-IGR-GS-non coding region-ORF (of foreign gene)-non coding region-RE recognition site 5'.

Similarly, in case a transcription cassette is to be introduced into a 3' non-coding region of a natural MV virus gene the cassette may be composed of: 3' RE recognition site-non coding region-ORF (of foreign gene)-non coding region-GE-IGR-GS-RE recognition site 5'.

The preparation of such transcription cassettes and the insertion thereof into a MV virus genome only involve routine molecular biologic techniques, such as exemplified in the literature references listed in Table 2 and in the present Examples. In particular, techniques such as site-directed-and PCR mutagenesis can be used for this purpose (Peeters et al., 1999, supra; Current Protocols in Molecular Biology, eds.: F. M. Ausubel et al., Wiley N.Y., 1995 edition, pages 8.5.1.-8.5.9; Kunkel et al., Methods in Enzymology Vol. 154, 376-382, 1987).

More in particular, a recombinant MV virus vector according to the present invention can be prepared by means of the well established "reverse genetics" method that enables the genetic modification of non-segmented, negative stranded RNA viruses of the order MV (reviewed for example by Conzelmann, K.K., Current Topics Microbiol. Immunol. 203, 1-41, 2004; and Walpita et al., FEMS Microbiol. Letters 244, 9-18, 2005).

In this method, an appropriate cell is co-transfected by a vector comprising a cDNA molecule comprising a nucleotide sequence that encodes a full length genome, or, preferably, an antigenome (positive sense) of a MV virus, and one or more vectors comprising the cDNA molecules comprising nucleotide sequences that encode the required support proteins, under conditions sufficient to permit transcription and co-expression of the MV (anti)genome and support proteins and the production of a recombinant MV vector. In this method, the said nucleic acid molecule encoding the full length MV virus (anti)genome comprises an additional transcription unit as defined above.

With vector is meant a replicon, such as a plasmid, phage or cosmid, to which another DNA segment may be attached so as to bring about the replication of the attached DNA segment and its transcription and/or expression in a cell transfected with this vector.

Preferably, the vector for the transcription of the full length genome is a plasmid that comprises a cDNA sequence encoding the (anti)genome of the MV virus, flanked by a T7 polymerase promoter at its 5' end and a (hepatitis delta) ribozyme sequence at its 3' end, although a T3 or SP6 RNA polymerase promoter can also be used.

For the intra-cellular expression of the appropriate support proteins use is made, preferably, of plasmids comprising the cDNA sequence encoding these proteins, under the control of appropriate expression control sequences, e.g. a T7 polymerase promoter.

In a particularly preferred method for the preparation of a recombinant MV virus vector according to the present invention, expression plasmids are used that encode the N (or NP), P and L proteins of the MV virus.

The amounts or ratios of transfected support plasmids to be used in this reverse genetic technology cover a broad range. Ratios for the support plasmids N:P:L may range from about 20:10:1 to 1:1:2 and efficient transfection protocols for each virus are known in the art.

An exact copy of the genomic RNA is made in a transfected cell by the combined action of the T7 RNA polymerase promoter and the ribozyme sequence, and this RNA is subsequently packaged and replicated by the viral support proteins supplied by the co-transfected expression plasmids.

It is preferred that a T7 polymerase enzyme is provided by a recombinant vaccinia virus that infects the transfected cell, in particular by the vaccinia virus vTF7-3, yet also other recombinant pox vectors, such as fowl pox virus, e.g. fpEFLT7pol, or other viral vectors may be used for the expression of T7 RNA polymerase.

Separation of the rescued virus from vaccinia virus can easily be accomplished by simple physical techniques, such as filtration. For rescue of Sendai virus or NDV, rescue can be achieved by inoculation of the supernatant of transfected cells in embryonated eggs.

In an even more preferred embodiment cell lines are used for the transfection of the transcription-and expression vectors that constitutively express the (T7) RNA polymerase and/or one or more of the required support proteins.

For example, rescue of Measles virus can be achieved in a human embryo kidney cell line, 293-3-46, that expresses both T7 RNA polymerase and Measles virus support proteins N and P (Radecke et al., EMBO J. 14, 5773-5784, 1995). Another very useful cell line that can be used advantageously in the present invention is based on BSR cells expressing the T7 RNA polymerae, i.e. cell line BSR-T7/5 (Buchholz et al., J. Virol. 73, 251-259, 1999).

Furthermore, more detailed information concerning the reverse genetics technology to be used herein for the preparation of a MV virus according to the present invention is disclosed in the review by Conzelmann, K.K. (supra) and Example 1.

The ability of recombinant MV virus vectors to stably express foreign genes has resulted in the development of vectors for both prophylactic and therapeutic applications.

In a recombinant MV virus vector according to the present invention the foreign gene can vary depending on the specific MV virus vector species and the application of the vector virus.

The foreign gene may encode an antigen of an (other) microbial pathogen (e.g. a virus, bacterium of parasite), especially the foreign gene encodes an antigen of a pathogen that is able to elicit a protective immune response.

For example, heterologous gene sequences that can be inserted into the virus vectors of the invention include, but are not limited to influenza virus glycoprotein genes, in particular, H5 and H7 hemagglutinin genes of avian influenza virus, genes derived from Infectious Bursal Disease Virus (IBDV), specifically VP2 of (IBDV), genes derived from Infectious Bronchitis Virus (IBV), feline leukemia virus, canine distemper virus, equine infectious anemia virus, rabies virus, *ehrlichia* organism, in particular *Ehrlichia canis*, respiratory syncytial viruses, parainfluenza viruses, human metapneumoviruses and measles virus.

Alternatively, the foreign gene may encode a polypeptide immune-modulator that is able to enhance or modulate the immune response to the virus infection, for example by co-expressing a cytokine such as an interleukin (e.g. IL-2, IL-12, IFN-γ, TNF-α or GM-CSF).

The order of MV includes both viruses that are able to replicate in humans and animals, or in both (e.g. rabies virus and Newcastle disease virus). Therefore, the foreign gene can be selected from a wide variety of human and veterinary microbial pathogens.

Although all MV viruses can be used as a vector virus in the present invention, in a preferred embodiment of the invention the recombinant MV virus vector is a virus of the family Rhabdoviridae, preferably of the genus *Lyssavirus* or *Novirhabdovirus*, more preferably of the species rabies virus or IHNV, respectively.

In an also preferred embodiment the recombinant MV virus is a virus of the family Paramyxoviridae, preferably of the genuses *Respovirus*, in particular the species hPIV3 or bPIV3, *Morbillivirus*, in particular the species CDV, *Pneumovirus*, in particular the species RSV and *Avulavirus*, in particular the species NDV.

In a particularly preferred embodiment of the present invention a recombinant MV virus vector is provided wherein the virus is Newcastle disease virus (NDV). As NDV is able to replicate in both humans and animals, in particular poultry, more in particular chickens, a recombinant NOV vector according to the invention may comprise a foreign gene that encodes an antigen of a pathogen, in particular of a respiratory pathogen, or an immune-modulator that is capable of eliciting an appropriate immune response in humans or any of these animals.

Reverse genetics methods for the genetic manipulation of NDV have been disclosed specifically for NOV by Peeters et al. (J. Virology 73, 5001-5009, 1999), Römer-Oberdörfer et al. (J. Gen. Virol. 80, 2987-2995, 1999), and in the review by Conzelmann, K. K. (supra). Furthermore, it is also known that NDV can be used as a vector for the expression of foreign genes, for example, for the eliciting of an immune response in animals infected with the NDV vector (Nakaya et al., 2001, supra) and Swayne et al., Avian Dis. 47, 1047-50, 2003).

A foreign gene can advantageously be introduced into a NDV genome at various positions as outlined in general for MV viruses above. In particular, in a recombinant NDV vector according to the invention, a foreign gene (as part of an appropriate transcription unit) can be inserted between the following NDV genes: NP-P, P-M, M-F, F-HN, HN-L and at the 3' proximal-and 5' distal locus (Zhao et al., 2003, supra; Nakaya et al., 2001, supra), preferably in the 3' proximal, P-M, M-F and F-HN regions, the F-HN region being most preferred.

Furthermore, in a recombinant NDV vector according to the present invention the non-coding regions that flank the foreign gene can be derived from all naturally occurring NDV genes, in particular from the N, P, M, F or HN genes, the HN gene being preferred.

In a particular embodiment of the invention a recombinant NOV vector is provided wherein the additional transcription unit is located between the F-HN genes and the inserted foreign gene is flanked by the non-coding regions of the NDV HN gene.

More specifically, a NDV vector is provided wherein the 3'-and 5' NCR (and optionally the GS and GE sequence) have a nucleotide sequence as shown in SEQ ID. No. 1 and 2 or 3 and 4.

A recombinant NDV vector according to the present can advantageously be used to induce an immune response in poultry, in particular chickens, against other pathogens. Therefore, the recombinant NDV vector, preferably comprises a foreign gene that encodes a protective antigen of an avian pathogen, in particular of influenza virus, marek's disease virus (MDV), infectious laryngotracheitis virus (ILTV), infectious bronchitis virus (IBV), infectious bursal disease virus (IBDV), chicken anemia virus (CAV), reo virus, avian retro virus, fowl adeno virus, turkey rhinotracheitis virus (TRTV), *E. coli*, *Eimeria* species, *Cryptosporidia*, *Mycoplasms*, such as *M. gallinarum*, *M. synoviae* and *M. meleagridis*, Salmonella-, Campylobacter-, Ornithobacterium (ORT) or *Pasteurella* sp.

More preferably, the recombinant NDV vector comprises a foreign gene that encodes an antigen of AIV, MDV, ILTV, IBV, TRTV, *E. coli*, ORT or *Mycoplasma*.

In particular, the recombinant NDV vector mutant comprises a hemagglutinin (HA) gene of an influenza virus, preferably of an avian influenza virus (AIV), more preferably of a highly pathogenic H5 or H7 AIV.

In principle, the HA gene of all (avian) influenza strains can be used in this invention. The nucleotide sequences of many HA gene have been disclosed in the art and can be retrieved from nucleic acid sequence databases, such as GenBank or the EMBL database.

The hemagglutinin (HA) gene of the recently isolated, highly pathogenic H5N2 subtype AIV A/chicken/Italy/8/98 can advantageously be used as a foreign gene in the present invention as outlined above. The gene is reverse transcribed, cloned in the eukaryotic expression vector pcDNA3 (Invitrogen), and sequenced (Lüschow et al., Vaccine, vol. 19, p. 42494259, 2001, and GenBank Accession No. AJ305306). From the obtained expression plasmid pCD-HA5 the HA gene can be obtained by amplification by using specific primers that generate artificial RE recognition sites that allow insertion of the HA gene in NDV genomic sequences.

In a further embodiment, the HA gene of the highly pathogenic H7N1 subtype AIV A/chicken/Italy/44599 can be used as a foreign gene in the present invention as outlined above. The HA gene is reverse transcribed, and amplified by PCR. The 1711 bp product is cloned in the SmaI-digested vector pUC18 (Amersham) and sequenced (Veits et al., J. Gen. Virol. 84, 3343-3352, 2003; and GenBank Accession No. AJ580353).

In a particularly advantageous recombinant MV virus vector according to the present invention, the MV vector virus is attenuated, that is to say: the vector virus is not pathogenic for the target animal or exhibits a substantial reduction of virulence compared to the wild-type virus. Many MV viruses used herein as virus vectors have a long safety record as live attenuated vaccines such as the measles virus and NDV, whereas other viruses, such as SeV and VSV are considered non-pathogenic to humans. In addition, conventional techniques exist to obtain and screen for attenuated viruses that show a limited replication or infectivity potential. Such techniques include serial (cold) passaging the virus in a heterologous substrate and chemical mutagenesis.

A recombinant NDV vector according to the invention can be derived from any conventional ND vaccine strain. Examples of such suitable NDV strains present in commercially available ND vaccines are: Clone-30®, La Sota, Hitchner B1, NDW, C2 and AV4, Clone-30® being the preferred strain.

It has also been found by the present inventors that a recombinant MV virus vector according to the present invention is able to induce a protective immune response in animals.

Therefore, in another embodiment of this invention a vaccine against a microbial pathogen is provided that comprises a recombinant MV virus vector as defined above in a live or inactivated form, and a pharmaceutically acceptable carrier or diluent.

A vaccine according to the invention can be prepared by conventional methods such as those commonly used for the commercially available live-and inactivated MV virus vaccines.

Briefly, a susceptible substrate is inoculated with the recombinant MV virus vector and propagated until the virus has replicated to a desired titre after which the virus containing material is harvested. Subsequently, the harvested material is formulated into a pharmaceutical preparation with immunizing properties.

Every substrate which is able to support the replication of the recombinant MV virus vector can be used in the present invention. As a substrate host cells can be used from both prokaryotic-and eukaryotic origin, depending on the MV virus. Appropriate host cells may be vertebrate, e.g. primate cells. Suitable examples are; the human cell lines HEK, WI-38, MRC-5 or H-239, the simian cell line Vero, the rodent cell line CHO, BHK, the canine cell line MDCK or avian CEF or CEK cells.

A particularly suitable substrate on which a recombinant NDV vector according to the present invention can be propagated are SPF embryonated eggs. Embryonated eggs can be inoculated with, for example 0.2 ml NOV containing allantoic fluid comprising at least $10^{2.0}$ $EID_{50}$ per egg. Preferably, 9-to 11-day old embryonated eggs are inoculated with about $10^{5.0}$ EID50 and subsequently incubated at 37° C. for 2-4 days. After 2-4 days the ND virus product can be harvested preferably by collecting the allantoic fluid. The fluid can be centrifuged thereafter for 10 min. at 2500 g followed by filtering the supernatant through a filter (100 μm).

The vaccine according to the invention comprises the recombinant MV virus vector together with a pharmaceutically acceptable carrier or diluent customaryly used for such compositions.

The vaccine containing the live virus can be prepared and marketed in the form of a suspension or in a lyophilized form. Carriers include stabilizers, preservatives, and buffers. Diluents include water, aqueous buffer and polyols.

In another aspect of the present invention a vaccine is provided comprising the recombinant MV virus vector in an inactivated form. The major advantages of an inactivated vaccine are its safety and the high levels of protective antibodies of long duration that can be induced.

The aim of inactivation of the viruses harvested after the propagation step is to eliminate reproduction of the viruses. In general this can be achieved by well known chemical or physical means.

If desired, the vaccine according to the invention may contain an adjuvant. Examples of suitable compounds and compositions with adjuvant activity for this purpose are aluminum hydroxide, -phosphate or -oxide, oil-in-water or water-in-oil emulsion based on, for example a mineral oil, such as BAYOL F® or MARCOL 52® or a vegetable oil such as vitamin E acetate, and saponins.

The administration of a vaccine according to the invention may be by any of the well known effective forms and may depend on the type of MV virus vector. Suitable modes of administration include, parenteral-, intranasal, oral and spray vaccination.

A NDV vector vaccine according to the invention is preferably administered by the inexpensive mass application techniques commonly used for NDV vaccination. For NDV vaccination these techniques include drinking water and spray vaccination.

A vaccine according to the invention comprises an effective dosage of the recombinant MV virus vector as the active component, i.e. an amount of immunizing MV virus material that will induce immunity in the vaccinated birds against challenge by a virulent microbial organism. Immunity is defined herein as the induction of a significantly higher level of protection in a population of humans or animals against mortality and clinical symptoms after vaccination, compared to an unvaccinated group. In particular, the vaccine according to the invention protects a large proportion of vaccinated humans or animals against the occurrence of clinical symptoms of the disease and mortality.

Typically, the live vaccine can be administered in a dose of $10^{2.0}$-$10^{8.0}$ tissue culture/embryo infectious dose (TC/$EID_{50}$), preferably in a dose ranging from $10^{4.0}$-$10^{7.0}$ $TC/EID_{50}$. Inactivated vaccines may contain the antigenic equivalent of $10^{4.0}$-$10^{9.0}$ $TC/EID_{50}$.

The invention also includes combination vaccines comprising, in addition to the recombinant MV virus vector according to the invention, a vaccine strain capable of inducing protection against a further pathogen.

EXAMPLES

Example 1

Generation of a Recombinant MV Virus Vector Expressing an Avian Influenza Virus HA Gene (NDV/AIVH5)

Viruses and Cells

Rescued recombinant NDV and the influenza virus isolate A/chicken/Italy/8/98 were propagated in specific pathogen free (SPF) 10-day-old embryonated chicken eggs. The velogenic NDV strain Herts 33156 and the NDV Clone 30 vaccine (Nobilis®) were used.

BSR-T7/5 cells stably expressing phage T7 RNA polymerase were used to recover infectious NDV from cDNA.

Construction of cDNA encoding NDV Antigenomic RNA Containing the AIV H5 Gene

The numbering in brackets as used herein to identify nucleotide positions on the NDV genome and amino acid residues in the NDV proteins is as described by Römer-Oberdörfer et al.(J. Gen. Virol. 80, 2987-2995, 1999, EMBL accession no. Y18898).

Figure 1A:
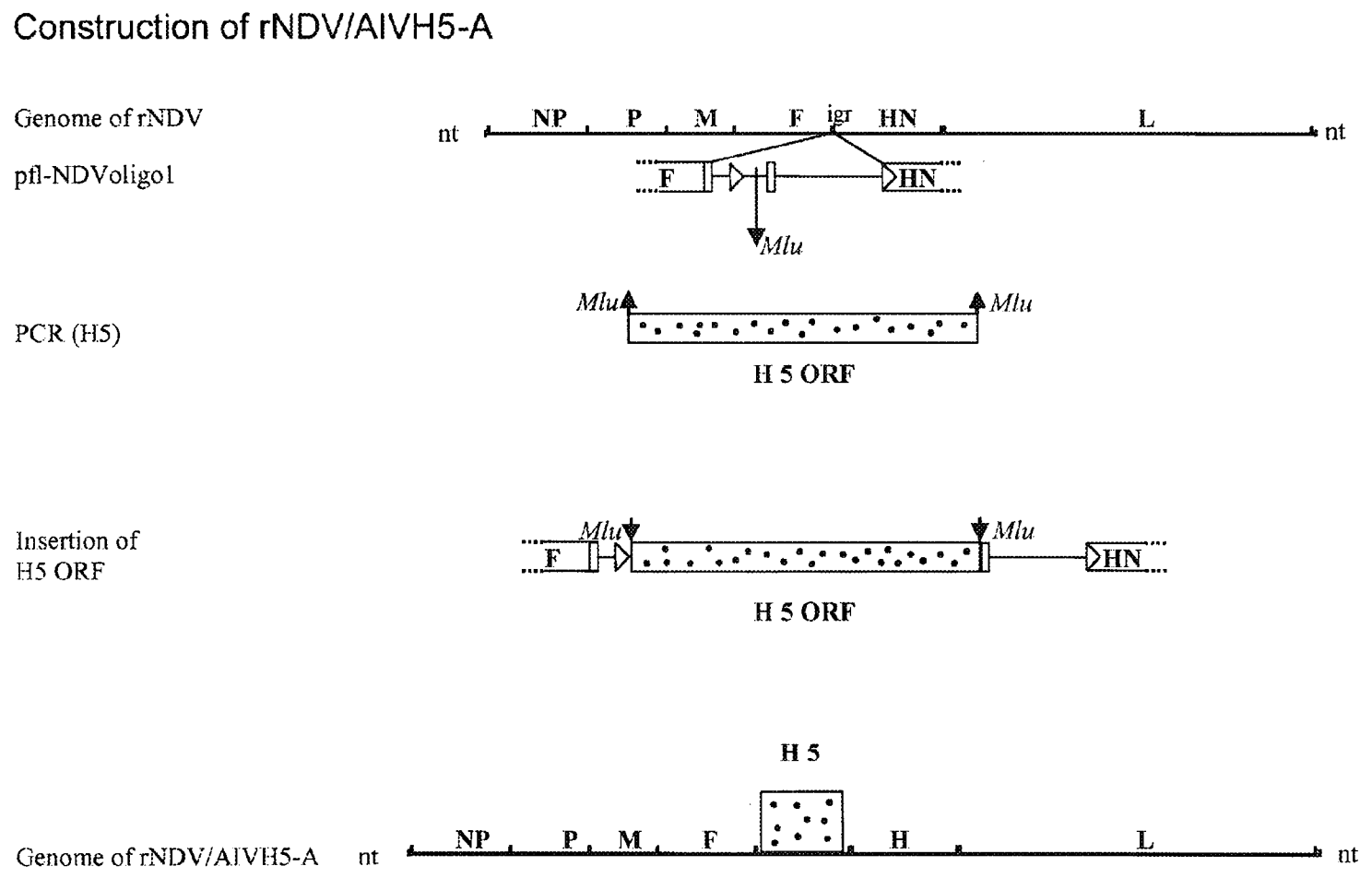

The plasmid pfINDV, expressing the full-length antigenomic RNA of Clone 30 (Romer-Oberdorfer et al., supra) was used to introduce the AIV H5 gene which had been amplified from plasmid pCD-HA5 (Luschow et al., supra) by specific primers with artificial MluI restriction sites (PH5F1:5'-cta a acgcgtaa aat gga gaa aat agt gc 3' (SEQ ID no. 5) and PH5R1: 5'-tcg gacgcgttt aaa tgc aaa ttc tgc act g-3' (SEQ ID no. 6), MluI sites are underlined) for rNDV/AIVH5-A and with NcoI or AflII sites (PH5F2:5'-cct tccatggag aaa ata gtg ctt c-3' (SEQ ID no. 7) and PH5R2: 5'-cct ccttaagta taa ttg act caa tta aat gca aat tct gca ctg caa tga tcc-3' (SEQ ID no. 8), restriction sites are underlined) for rNDV/AIVH5-B. The introduction of H5 into the Clone 30 antigenome (FIG. 1A) was done using the MluI sites as previously described for the GFP insertion (Engel-Herbert et al., J. Virol. Methods 108, 19-28, 2003). Briefly, for construction of the full-length plasmid pfINDV/AIVH5-A the H5 ORF was amplified with primers containing artificial MluI sites (see above) which were used to insert the H5 ORF into the minimal gene cassette between the F and HN gene of NDV (FIG. 1A).

Construction of the full-length plasmid containing the AIV H5 gene for generation of rNDV/AIVH5-B is given in FIG. 1B. Mutagenesis reactions were done using the QUICK CHANGE II XL site directed mutagenesis kit (Stratagene). To this end, a pUC 18 plasmid (pUCNDV1) containing the NotI/BsiWI-fragment (nt 4953-8852) of Clone 30 genome and following primers were used: MP1 (5'-gac aac agt cct caa cca tgg acc gcg cog-3') (SEQ ID NO: 9) and MP2 (5'-ctg gct agt tga gtc aat tct taa gga gtt gga aag atg gc-3') (SEQ ID NO: 10) for mutagenesis A (FIG. 1B) resulting in the plasmid pUCNDV1a with newly created NcoI and AflII sites (restriction sites in primers are underlined). After digestion with NcoI and AflII the HN ORF of Clone 30 was substituted by the amplified AIV H5 ORF. For mutagenesis B to create SgfI-and SnaBI-sites in the intergenic region in front of the L gene of pUCNDVH5 resulting in pUCNDV/AIVH5-1 b (FIG. 1B) primers MP3 (5'-caa aac agc tca tgg tac gta ata cgg gta gga cat gg-3') (SEQ ID NO: 11) and MP4 (5'-gta agt ggc aat gcg atc gca ggc aaa aca gct cat gg-3') (SEQ ID NO: 12) were used. Mutagenesis C was done with MP3 and MP5 (5'-gaa aaa act acc ggc gat cgc tga cca aag gac gat ata cgg g-3') (SEQ ID NO: 13) resulting in plasmid pUCNDV1c to obtain SgfI-and SnaBI-sites which were used for the introduction of the Clone 30 HN gene into the intergenic region in front of the L gene in plasmid pUCNDVH5_1b. Finally, the NotI/BsiWI-fragment of pfINDV-1 was substituted by the NotI/BsiWI-fragment of pUCNDVH5_1c (FIG. 1B). The lengths of the new generated full-length genomes represent a multiple of six (16938 nt for rNDV/AIVH5-A and 17196 nt for rNDV/AIVH5-B).

Transfection and Virus Propagation

Transfection experiments, virus propagation and confirmation of the recovery of infectious virus were carried out as described previously (Römer-Oberdörfer et al., supra; Engel-Herbert et al., supra). The only difference was that a total amount of DNA of 20 µg (10 µg full-length genome containing plasmid, 6 µg pCiteNP, 2 µg pCiteP and 2 µg pCiteL) was used for transfection.

Results

The AIV H5 open reading frame was inserted between the F and HN genes of the previously described plasmid pfINDV (Römer-Oberdörfer et al., supra). To this end, the AIV H5 ORF of the AIV isolate A/chicken/Italy/8/98 (H5N2) was amplified from plasmid pCD-HA5 (Luschow et al., supra) by specific primers with MluI restriction sites which were used for insertion of the AIV H5 ORF into the singular MluI restriction site of pfINDVoligo1; (Engel-Herbert et al., supra) resulting in plasmid pfINDV/AIVH5-A (FIG. 1A). In this construct the AIV H5 ORF was flanked by artificial gene start (GS) and gene end (GE) sequences in the intergenic region between the F and HN genes of NDV. For construction of full-length plasmid pfINDV/AIVH5-B the HN ORF of plasmid pUCNDV1a was substituted by the amplified H5 ORF as a NcoI/AflII-fragment (FIG. 1B). In the resulting plasmid pUCNDVH5 SgfI and SnaBI restriction sites were created in the intergenic region downstream of the H5 gene resulting in plasmid pUCNDVH5_1b (FIG. 1B). The created SgfI and SnaBI restriction sites were used to introduce the HN gene from plasmid pUCNDV1c, in which the HN gene was also flanked by SgfI and SnaBI restriction sites (FIG. 1B). Finally, the resulted plasmid pUCNDVH5_1c was used to replace the NotI/BsWI-fragment of pfINDV (FIG. 1B). The constructed pfINDV/AIVH5-B differs from plasmid pfINDV/AIVH5-A since the noncoding regions of NDV HN were additionally inserted between the transcriptional control elements (GS, GE) and the H5 ORF.

NDV recombinants rNDV/AIVH5-A and rNDV/AIVH5-B were recovered from BSR-T7/5 cells transfected with the respective full-length cDNA and support plasmids as previously described (Römer-Oberdörfer et al., supra; Engel-Herbert et al., supra). For virus recovery the transfection supernatants were injected into the allantoic cavities of 10-day-old embryonated chicken eggs and incubated for 5 days. The allantoic fluid was harvested and analyzed for presence of virus by hemagglutination test or indirect immunofluorescence (IF). Virus-containing allantoic fluids were used for a second egg passage for further virus propagation. The presence of the inserted H5 gene in the viral genomes of rNDV/AIVH5-A and rNDV/AIVH5-B was confirmed by reverse transcription-PCR and sequencing (data not shown). FIGS. 2A and 2B show the nucleotide sequence of regions flanking the HN ORF in NDV and of the H5 ORF in the NDV vector.

Example 2

In Vitro Characterization of the NDV/AIVH5 Vector

RNA Analyses

CEF cells were infected with NDV Clone 30, rNDV/AIVH5-A, rNDV/AIVH5-B and AIV A/chicken/Italy/8/98 (H5N2) at a multiplicity of infection (MOI) of 10 per cell and incubated for 8 h at 37° C. Total RNA of infected and uninfected cells was prepared, separated in denaturing agarose gels and hybridized with radiolabeled cRNA's The plasmids pCD-HA5 and pCD-NDVHN which contain the open reading frame of AIV A/chicken/Italy/8198 (H5N2) H5 and NDV Clone 30 HN, respectively, were used for in vitro transcription of $^{32}$P-labeled cRNA (SP6/T7 Transcription kit, Roche).

To verify transcription of the inserted AIV H5 gene in rNDV/AIVH5-A and -B Northern blot analyses were performed with total RNA of NDV/AIVH5 recombinant infected primary chicken embryo fibroblasts. RNA preparation of NDV Clone 30 and AIV A/chicken/Italy/8/98 (H5N2) infected cells were used as controls. Transcription of the inserted AIV H5 gene was detected for rNDV/AIVH5-A as well as for rNDV/AIVH5-B with gene-specific antisense cRNA (FIG. 3). It can be observed that the AIV-H5B transcript is extended by about 81 nt and is more abundantly present than the AIV-H5A transcript.

Western Blot Analyses

CEK cells were infected with NDV Clone 30, rNDV/AIVH5-A, rNDV/AIVH5-B and AIV A/chicken/Italy/8/98 (H5N2) and incubated for 20 h at 37° C. Lysates of infected and of uninfected control cells were separated by SDS-PAGE (ca. $10^4$ cells per lane), and transferred to nitrocellulose filters (TRANS-BLOT SD cell, Bio-Rad). Blots were incubated with a polyclonal rabbit antiserum against NDV, or a polyclonal chicken antiserum against AIV of the subtype H5 at dilutions of 1:20000 and 1:2500, respectively. Binding of peroxidase-conjugated species-specific secondary antibodies was detected by chemiluminescence using SUPERSIGNAL West Pico Chemifuminescent Substrate (Pierce) on X-ray films HYPERFILM MP, Amersham).

In Western blot analyses the H5 protein was detectable only in rNDV/AIVH5-B infected cells. The AIV subtype H5-specific antiserum detected two prominent proteins of approximately 70 and 50 kDa and a barely visible protein of ca. 25 kDa, which were not found in NDV Clone 30 infected cells (FIG. 4).

Indirect Immunofluorescence (IF) Tests

For indirect IF tests CEF cells were infected at low MOI with NDV Clone 30, rNDV/AIVH5-A, rNDV/AIVH5-B and AIV A/chicken/Italy/8/98 (H5N2) for 20 h. After fixation with methanol and acetone (1:1) the cells were subsequently incubated with either a polyclonal rabbit antiserum against NDV or a polyclonal chicken antiserum against AIV of subtype H5 at dilutions of 1:3000 and 1:100 respectively. After incubation with $F(ab)_2$ fragment of anti rabbit IgG and fluorescein-conjugated anti chicken IgG antibodies samples were analyzed by conventional fluorescence microscopy.

H5 expression was examined by indirect IF test of infected CEF cells. After incubation with a NDV-specific antiserum pronounced fluorescence was detectable in cells infected with NDV Clone 30, rNDV/AIVH5-A and rNDV/AIVH5-B, but not in cells infected with AIV A/chicken/Italy/8/98 (H5N2) or in non infected cells (FIG. 5, right panel). Incubation with an AIV subtype H5-specific antiserum showed a marked fluorescence in AIV infected cells. Comparing the two recombinants, rNDV/AIVH5-B showed a more intense H5-specific fluorescence than rNDV/AIVH5-A indicating a higher expression level of the H5 protein (FIG. 5, left panel).

Immunoelectron Microscopy

The viral particles were adsorbed to formvar coated copper grids for 7 min. The grids were washed four times with PBS containing 0.5% bovine serum albumin and subsequently incubated with a NDV-specific or a AIV subtype H5-specific antiserum for 45 min. After several washings with PB, grids were incubated for further 45 min with protein A gold (10 nm, PAG 10, Biocell International) or rabbit anti-chicken gold (10 nm, RCHL 10, Biocell International). After final washings with PB the virus particles were contrasted with phosphotungstic acid (PTA, pH 7.2) and examined with an electron microscope.

When virions of NDV Clone 30 or rNDV/AIVH5-A were examined, staining was observed only with NDV-specific antiserum. In contrast, for rNDV/AIVH5-B staining was observed using antisera against NDV and also by using antisera against AIV, demonstrating that virions of rNDV/AIVH5-B contain hemagglutinin H5. Gold particles were found predominantly along the surface of rNDV/AIVH5-B virions, indicating that the hemagglutinin was anchored in the viral membrane.

Example 3

In Vivo Characterization of the NDV/AIVH5 Vector

Evaluation of Protection by Recombinant rNDV/AIVH5-A and rNDV/AIVH5-B:

One-day-old chickens were randomly assigned to two groups and vaccinated oculonasally with $10^6$ $EID_{50}$ of rNDV/AIVH5-A or with commercial NOV Clone 30 vaccine (Nobilis®, Intervet, NL) via spray. At 28 days of age a second immunization was administrated the same way. On day 12 after the second immunization blood was collected for assessing presence of NDV and AIVH5 antibodies by HI test. Two weeks after the second vaccination the immunized groups were divided and one part of each group was challenged oculonasally with $10^8$ $EID_{50}$ of the highly pathogenic AIV isolate A/chicken/Italy/8/98 (H5N2). The remaining chickens were used to evaluate the protective efficacy of the vaccines against velogenic NOV. Therefore the birds and additional control animals received $10^{5.3}$ $EID_{50}$ of NOV strain Herts 33/56 intramuscularly.

After immunization and challenge infection all birds were observed daily for a period of 10 days for clinical signs and classified as healthy (0), ill (1; one of the following signs: respiratory signs, depression, diarrhea, cyanosis, oedema, nervous signs), severely ill (2; more than one of the following signs: respiratory signs, depression, diarrhea, cyanosis, oedema, nervous signs), or dead (3). A clinical score was calculated which represents the mean value of all chickens per group for this period. Finally, three weeks after challenge blood samples were taken from all surviving animals in order to evaluate antibody titers against AIV and NDV.

The NDV recombinant rNDV/AIVH5-B was tested in a separate animal trial of nearly identical experimental design. The only differences were that immunizations with $10^6$ $EID_{50}$ of either rNDV/AIVH5-B or NDV Clone 30 vaccine were administrated in both groups oculonasally and no NDV challenge infection was performed.

Figure 6:
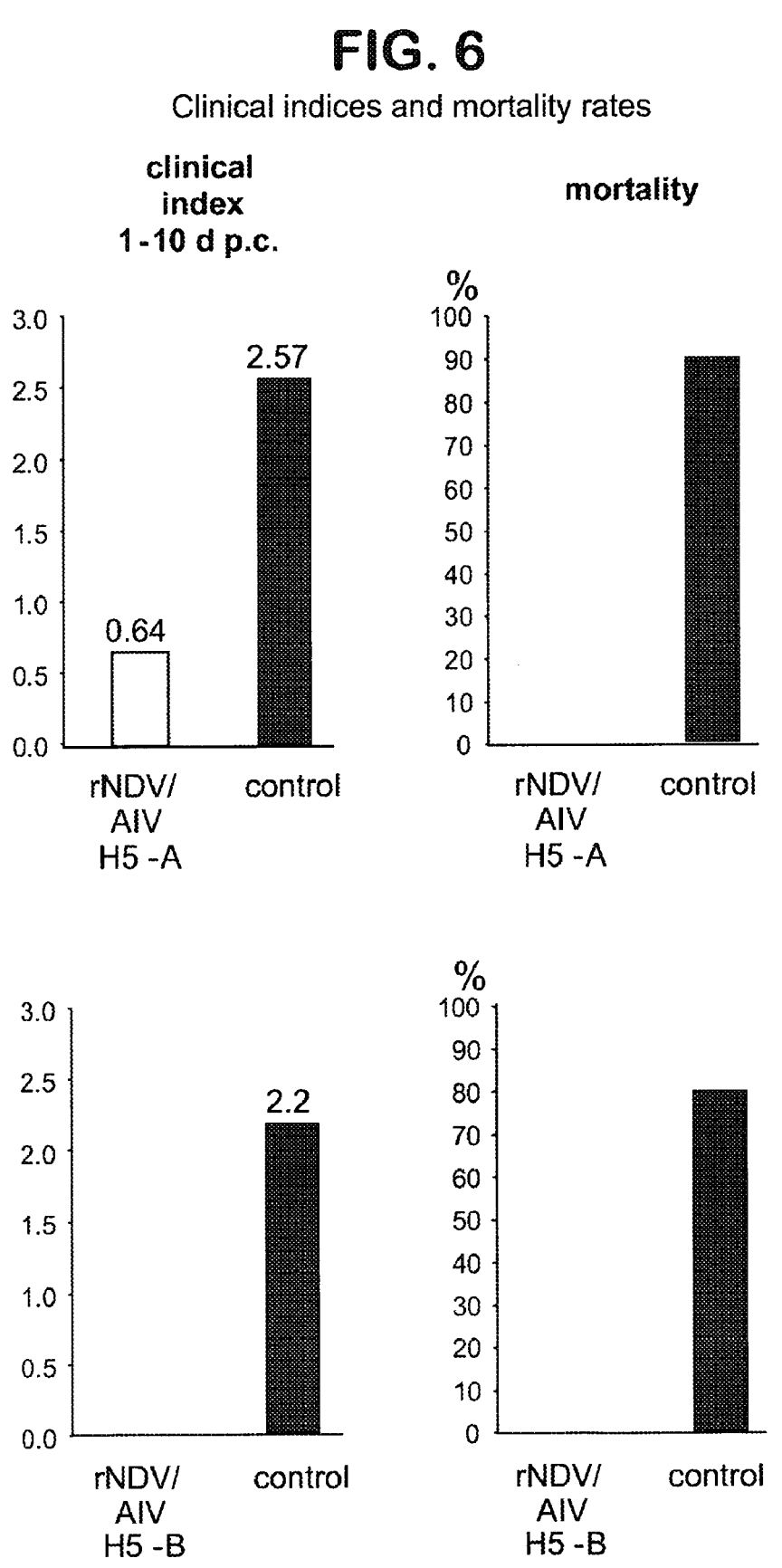

All data of these experiments are summarized in Table 4 and FIG. 6. Sera of the immunized chickens were analyzed by HI test three weeks after vaccination, but no HA-specific serum antibodies could be detected in both cases. All animals of both groups developed NDV-specific antibodies at high levels already after the first immunization (mean HI-titers of $2^6$-$2^7$) the animals were fully protected against an infection with velogenic NDV, whereas all control animals died within 4 days exhibiting typical signs of ND. As expected, the AIV challenge infection caused severe disease in NDV Clone 30 immunized chickens with a mortality rate of 90%. Animals of the rNDV/AIVH5A immunized group survived a lethal dose of highly pathogenic AIV, but all chickens exhibited varying signs of avian influenza with a clinical score of 0.64 indicating significant yet partial protection. However, chickens immunized with rNDV/AIVH5-B were completely protected against any signs of disease after infection with a highly pathogenic avian influenza A virus.

TABLE 4

Summary of animal experiments rNDV/AIVH5-A and rNDV/AIVH5-B

| 1. Immunization | Time scale[1] | rNDV/AIVH5-A oculon. | Clone 30 spray | control | Time scale[1] | rNDV/AIVH5-B oculon. | Clone 30 oculon. |
|---|---|---|---|---|---|---|---|
| $EID_{50}$/animal | | $10^{5.7}$ | $10^{6.0}$ | — | | $10^{6.0}$ | $10^{6.0}$ |
| Mortality | 1.-10. d pi | 0/24 | 0/34 | — | 1.-10. d pi | 0/5 | 0/5 |
| Morbidity | 1.-10. d pi | 6/24 | 5/34 | — | 1.-10. d pi | 0/5 | 0/5 |
| clinical score[2] | | 0.034 | 0.016 | | | 0 | 0 |
| NDV-specific Ab | 17 d pi | 22/22 | 34/34 | | 21 d pi | 5/5 | 5/5 |
| Ø HI-titer | | $2^{5.6}$ | $2^{7.2}$ | | | $2^{5.6}$ | $2^{7.6}$ |
| HA-specific Ab | 17 d pi | 22/22 | 34/34 | | 21 d pi | 5/5 | 5/5 |
| Ø HI-titer | | 0 | 0 | | | 0 | 0 |

| 2. Immunization | 28 d pi | rNDV/AIVH5-A oculon. | Clone 30 spray | control | 28 d pi | rNDV/AIVH5-B oculon. | Clone 30 oculon. |
|---|---|---|---|---|---|---|---|
| $EID_{50}$/animal | | $10^{6.0}$ | $10^{6.0}$ | — | | $10^{6.0}$ | $10^{6.0}$ |
| Mortality | 1-10. d pb | 0/22 | 0/24 | — | 1-10. d pb | 0/5 | 0/5 |
| Morbidity | 1-10. d pb | 4/22 | 3/24 | — | 1-10. d pb | 0/5 | 0/5 |
| clinical score[2] | | 0.023 | 0.017 | | | 0 | 0 |
| NDV-specific Ab | 12 d pb | 21/21 | 24/24 | 5/5 | 12 d pb | 5/5 | 5/5 |
| Ø HI-titer | | $2^{7.3}$ | $2^{6.8}$ | 0 | | $2^{6.0}$ | $2^{7.8}$ |
| HA-specific Ab | 12 d pb | 2/21 | 24/24 | 5/5 | 12 d pb | 5/5 | 5/5 |
| Ø HI-titer | | $2^3$ | 0 | 0 | | 0 | 0 |

| Challenge | | NDV Herts 33/56 | | | | | |
|---|---|---|---|---|---|---|---|
| $EID_{50}$/animal | 14 d pb | $10^{5.3}$ | | | | | |
| Mortality | 3.-4. d pc | 0/10 | 0/10 | 5/5 | | | |
| Morbidity | 1.-10. d pc | 4/10 | 5/10 | 5/5 | | | |
| clinical score[2] | | 0.04 | 0.05 | 2.4 | | | |
| NDV-specific Ab | 20 d pc | 10/10 | 10/10 | † | | | |
| Ø HI-titer | | $2^{8.9}$ | $2^{9.2}$ | | | | |

| Challenge | | AIV A/ch/Italy/8/98 (H5N2) | | | | AIV A/ch/Italy/8/98 (H5N2) | |
|---|---|---|---|---|---|---|---|
| $EID_{50}$/animal | 14 d pb | $10^{8.0}$ | | | 14 d pb | $10^{7.7}$ | |
| Mortality | 3.-6. d pc | 0/10 | 9/10 | | 3.-4. d pc | 0/5 | 4/5 |
| Morbidity | 1.-10. d pc | 10/10 | 10/10 | | 1.-10. d pc | 0/5 | 5/5 |
| clinical score[2] | | 0.64 | 2.57 | | | 0 | 2.2 |
| AIV-specific Ab | 20 d pc | 10/10 | 1/1 | | 24 d pc | 5/5 | 1/1 |
| Ø HI-titer | | $2^{6.5}$ | $2^{9.0}$ | | | $2^{8.0}$ | $2^{11}$ |

Example 4

Construction of an NDV/AIV-H5 Vector with Flanking ncr from the NDV F-Gene

Using essentially the same methods and materials as described above (Engel-Herbert et al., supra), an NDV vector construct was made carrying the H5 AIV gene in between the F and HN genes of the previously described plasmid pfINDV (Römer-Oberdörfer et al., supra), but now the H5 insert was flanked with non-coding regions from the NDV F-gene. Briefly the Various Steps and Materials used were:

A pUC plasmid with the 1,6 kb NotI-PstI fragment of NDVH5 (pUCIRA) was mutated to create an MluI restriction enzyme site, using mutagenesis primers; pMPMLUIGRF-HNF (5'-ggt tgt aga tga cca aag gacaca tta cgg gta gaa cgg taa gag agg-3'; SEQ ID NO: 14) and pMPMLUIGRFHNR (5'-cct ctc tta ccg ttc tac ccg taa cgc gtc ctt tgg tca tct aca acc-3'; SEQ ID NO: 15) (MluI site underlined, with GS sequence in bold), resulting in plasmid pUCIRAMLU.

Two oligo's were annealed: OFVOF: 5'-agg acgcgt tac ggg tag aag aft ctg gat ccc ggt tgg cgc cct cca ggt gca gca cca tgg ag-3' (SEQ ID NO: 16, MluI site underlined) and OFVORL: 5'-ctc cat ggt gat gca cct gga ggg cgc caa ccg gga tcc aga tct ttc tac ccg taacacgtc ct-3' (SEQ ID NO: 17, Mtu I step underlined). Next these were digested with MluI and NcoI.

Digestion of the plasmid pUCIRAMLU with MluI and NcoI.

Ligation of the approximately 4,3 kb MluI-NcoI fragment of pUCIRAMLU with the MluI-NcoI digested OFVOF/OFVOR oligohybrid. The resulting plasmid was named pUCIRA2.

A pUC plasmid (pUCAROK) with the NotI-BsiWI fragment of NDV with the H5 orf instead of the HN orf and pUCIRA2 were digested with NcoI and SgfI and the NotI-NcoI fragment of pUCAROK was substituted by that of pUCIRA2, resulting in the plasmid pUCAROK2.

HF-PCR (Roche) was done to amplify the ncr of the NDV F gene behind the inserted F gene, using primers: PNCRF-HIF: 5'-ata cttaag ttc cct aat agt aat ttg tgt-3' (SEQ ID NO: 18, AflII site underlined), and PNCRFHIR. 5'-cac gcgatcgca ttg cca ctg tac att ttt tct taa ctc tct gaa ctg aca gac tac c-3' (SEQ ID NO: 19, SgfI site underlined), and plasmid pUCAROA (pUC with NotI-SpeI fragment of NDV). The resulting ~100 bp fragment was ligated into pGEMTeasy vector to give pGEM-Fncrhi plasmid.

pUCAROK2 and pGEMFncrhi plasmids were digested with AflII and SgfI to substitute the HN ncr behind H5 of plasmid pUCAROK2 by that of F from pGEMFncrhi. The resulting plasmid was named pUCAROK4.

In the last step the NotI-SgfI fragment of the NDVH5 plasmid was substituted by that of pUCAROK4 resulting in the new full-length plasmid E18C, comprising the AIV H5 gene inserted in the NDV vector between F and HN, and flanked by F-gene ncr's.

With the new constructs transfection experiments, rec virus propagation and confirmation of the recovery of infectious virus were carried out as described above. Next the virus was characterized biochemically and biologically.

Example 5

Generation of other NDV Vector Constructs and rec Viruses

Using similar techniques several other inserts were made in the NDV vector, using different inserted genes, and different insertion sites.

With the details already provided herein these are al within easy reach of the skilled persons' capabilities, therefore it suffices to present these in table form:

TABLE 5

Other NDV vector constructs according to the invention:

| Inserted gene | NDV insertion region | NDV flanking ncr region |
|---|---|---|
| AIV H5 | P-M | HN |
| AIV H5 | M-F | HN |
| AIV H7 | F-HN | HN |
| AIV N1 | F-HN | HN |
| AIV H5 | Before NP | HN |

Example 6

Generation of a Recombinant Rabies Virus Vector Expressing an EIAV Envelope Gene To demonstrate that the advantageous effects of the invention (the use of MV gene non-coding regions to increase the expression and/or presentation of foreign proteins in rec MV virions) expands beyond the family Paramyxoviridae, rabies virus—a member of the family Rhabdoviridae—was used as a vector to express an envelope protein derived from an unrelated virus, equine infectious anemia virus (EIAV).

In this example the construction is described of a rec rabies vector virus comprising the EIAV envelope protein, inserted between the rabies genes G and L, whereby the env gene is flanked by the ncr's from the rabies G-protein gene.

Subclones of rabies viruses were prepared in pBluescript® SK+ phagemid using the SAD-D29 full-length clone (Mebatsion, 2001, J. Virol., vol. 75, p. 11496-11502), which is referred here as ORA-D. To prepare a cloning vector, a pSK vector was first digested with SacI, blunted with Klenow enzyme, followed by digestion with HindIII and gel purification of the ~3 Kb fragment. The insert was prepared by digesting ORA-D with StuI and HindIII, purifying the resultant 1.3 kb fragment, and ligating into the prepared pSK vector to generate plasmid pNCR-b.

The pNCR-b plasmid was digested with BstII and HindIII and the ~4.0 kb fragment was purified and used for ligation with the oligo's BSSNH+ and BSSNH− (see Table 6) to create plasmid pSSNsc containing a minimum transcription cassette and ligation with oligos RABGNCR1-4 (Table 6) to generate the construct GNCR-b, containing non-coding regions in addition to the minimum transcription unit (FIG. 7).

The EIAV strain Wyoming env gene was obtained by amplification from a 2052 nt synthetic gene which had been codon-optimized, RNA splice sites removed (Cook, et al. 2005, Vet. Micro., vol. 108, p. 23-37), and truncated by 134 amino acids at the 3' coding region of the original gene.

TABLE 6

Oligo sequences used during the construction of rec rabies viruses

| Oligo-name | SEQ ID NO: | Oligo sequence (5' -> 3') |
|---|---|---|
| BSSNH+ | 20 | CTGGTGAAAAAAACTAACA-CCCCTGCTAGCA |
| BSSNH− | 21 | CGTTGACCACTTTTTTTGAT-TGTGGGGACGATCGTTCGA |
| RABGNCRoligo1 (*) | 22 | CTGGTGAAAAAAACTATTA-ACATCCCTCAAAAGACTCA-AGGATACGTACT |
| RABGNCRoligo2 | 23 | GTATCCTTGAGTCTTTTGAG-GGATGTTAATAGTTTTTTTC-ACCAGTTGC |
| RABGNCRoligo3 | 24 | GGCCGTCCTTTCAACGATC-CAAGTCCTGAAGATCACCT-CCCCTTGGGGGA |
| RABGNCRoligo4 | 25 | AGCTTCCCCCAAGGGGAGG-TGATCTTCAGGACTTGGATC-GTTGAAAGGACGGCCAGTAC |
| ElAsynCDF | 26 | ATGGTGTCCATCGCCTTCTA |
| ElAsynCDstopR | 27 | TCAGTGTATGTTGTGTTGGGC |

(*) 3 nt changed from ORA-D original : GGAAAG GGACTGG, to: GGATAC GTACTGG

The amplified env gene was kinased and inserted into subclones as follows: a ~2.0 Kb amplicon, engineered to represent the entire truncated EIAV envelope protein, was generated using the primer set ElAsynCDF+ElAsynCDstopR (see Table 6). The amplicon was inserted into subclone GNCR-b which had been predigested with SnaBI and dephosphorylated to generate the recombinant plasmid pGNCR-b:envG. The ~2.0 Kb fragment was also inserted into the SSNsc subclone which had been predigested with NheI, blunt-ended and dephosphorylated to generate the recombinant plasmid pSSNsc:env.

Each recombinant construct was digested with SphI and HindIII and ligated into the SSNsc subclone, which was SphI/HindIII predigested and dephosphorylated with CIAP. After returning to the SSNsc subclone, the modified inserts were returned to the ORA-D backbone by digestion with SphI and MluI to generate the recombinant rabies viruses RV-env and RV-envG (FIG. 8). The 5' and 3' ends of the constructs were verified by sequence analysis using Big-Dye® Terminator Cycle Sequencing chemistry (Applied Biosystems) and analyzed using an Applied Biosystems 3100-Avant Capillary Electrophoresis Sequencer.

The construction of a full length cDNA clone based on the modified SAD rabies strain ORA-D and generation of a recombinant rabies virus has been described (Schnell et al., 1994, EMBO J., vol. 13, p. 4195-4203; Mebatsion, 2001, supra). Each recombinant rabies virus was transfected into BSR cells as previously described (Schnell, et al., 1994, supra) using Mirus Trans-IT-LT1. Three days post-transfection, cells and supernatant were harvested and passed. Subsequent passages were by supernatant only, using an estimated moi of 0.5. Each recombinant virus was passaged a minimum of five times to verify stability.

BSR cells infected with recombinant rabies were fixed ~40 hours post-infection. These were analyzed by direct immunofluorescence using FITC Anti-Rabies Monoclonal Globulin (FDI Diagnostics Inc.) or using anti-EIAV polyclonal horse sera. In 10-fold serial dilutions, the ratio of infected cells producing rabies virus were also compared to infected cells expressing EIAV env to monitor virus stability and recombinant antigen expression.

Recombinant rabies viruses from pass five were inoculated into T-75 flasks with fresh BSR cells at an moi of 0.01. 24-hours post infection, media was changed to serum-free. Supernatant was collected and clarified by centrifugation (10,000×g) at 72 hours post-infection. Viral supernatants were purified by sucrose gradients to analyze purified virions.

Purified virions and total infected cellular protein were combined with 2× Laemmli reducing sample buffer and placed in boiling water for 5-10 minutes. Samples were loaded onto a 10% Tris-HCL acrylamide gel (Bio-Rad) in 1×SDS-PAGE Running Buffer. SDS-PAGE gels were run at 20 mA until the dye-front was near or at the bottom of the gel. The separated proteins were transferred onto Immobilon-P (PVDF) membrane (IPVH10100, Immobilon) by blotting at 225 mA for 45 minutes. Blots were incubated in blocking buffer (PBS-Tween 20+1% dry non-fat milk) for one hour at room temperature and then rinsed 3 times for 5 minutes in PBS-Tween 20. Rabies expression was detected using rabbit anti-rabies polyclonal sera directed against rabies glycoprotein and nucleoprotein diluted 1:20000 and 1:2000, respectively, in blocking buffer.

Simultaneously, EIAV env expression was detected using anti-EIAV polyclonal horse sera diluted 1:500 in blocking buffer. Blots were incubated for one hour at room temperature and then rinsed 3 times for 5 minutes in PBS-Tween20. Blots were placed in HRP labeled conjugate goat anti-rabbit IgG (H+L) (KPL) and HRP labeled conjugate goat anti-horse IgG (H+L) (Bethyl Labs), each diluted 1:2000 in blocking buffer and incubated for one hour at room temperature. Blots were then rinsed 3×5 minutes in PBS-Tween20. Blots were incubated in TMB membrane peroxidase substrate (KPL) until development was complete, approximately 1-3 minutes. Blots were placed in distilled water to stop the reaction.

Figure 9:
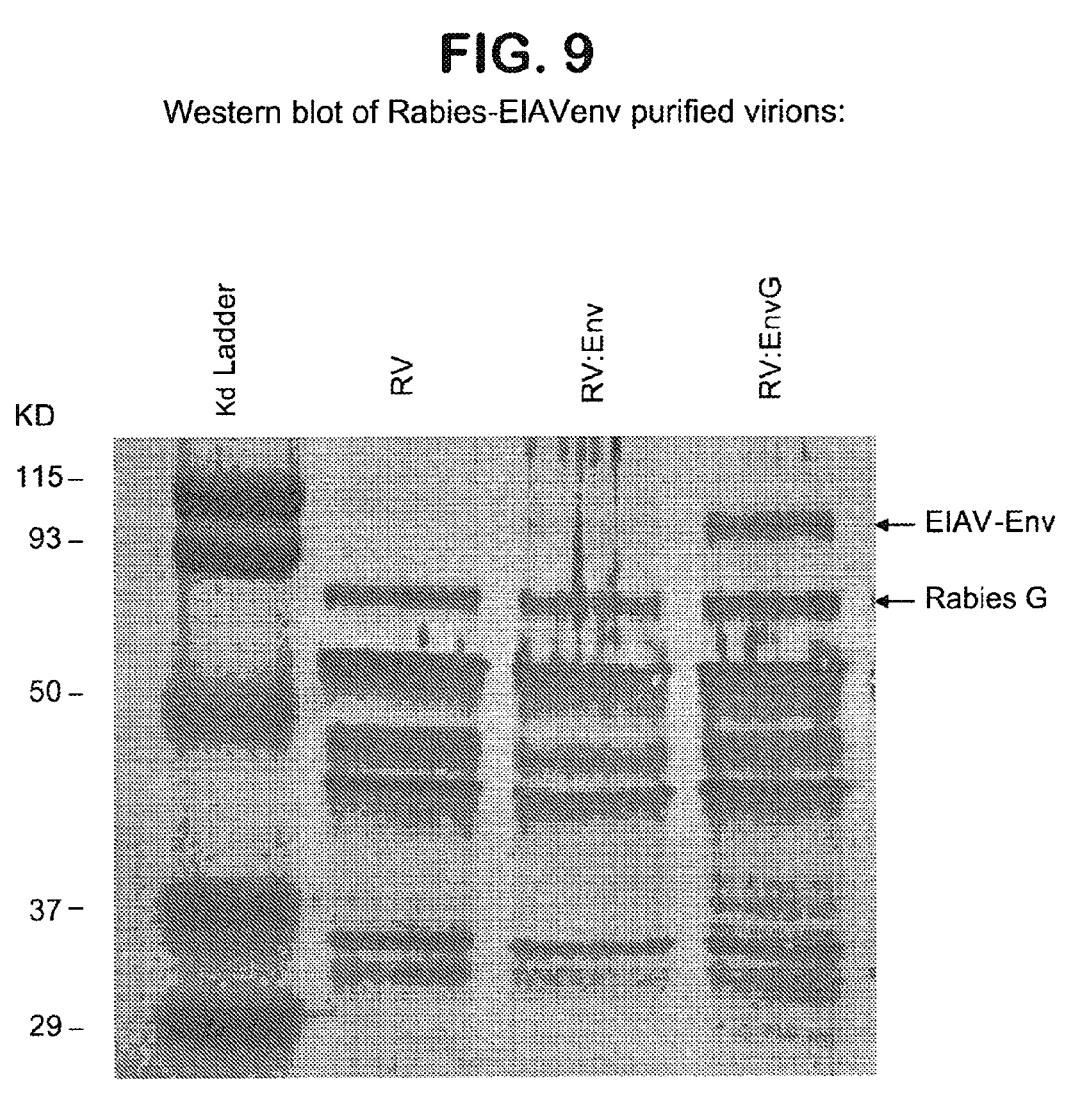

A typical result of such a Western blot experiment is shown in FIG. 9, and demonstrates the protein composition of recombinant rabies viruses expressing EIAV envelope protein.

Lane 1: Broad-range MW ladder (Bio-Rad);
Lane 2: ORA-D backbone virus;
Lane 3: RV-env, comprising the EIAV-env gene, inserted between the rabies G and L genes, without flanking ncr's
Lane 4: RV-envG, comprising the EIAV-env gene, flanked by the ncr regions of the rabies virus G-protein.

Both recombinant rabies viruses yielded comparable infectious titer and stably expressed the EIAV-env gene insert after multiple passage in vitro.

However, despite subjecting comparable amounts of virions to the Western blot, recombinant RV-env, constructed in the customary way (thus without flanking ncr's) exhibited only a very weak band corresponding to the EIAV-env protein; whereas the recombinant virus RV-envG, that had the G-protein non-coding regions flanking the inserted EIAV-env protein, was expressed at a much higher rate: FIG. 9, compare the band for the env protein in lanes 3-4.

As the constructs and inserts of RV-envG and RV-env are otherwise identical, this is strong proof that the non-coding regions have a positive effect in promoting high level of foreign protein production and immune-presentation.

---

The invention claimed is:

1. A recombinant Mononegavirales virus vector harboring an additional transcription unit comprising a foreign gene operatively linked with an upstream Mononegavirales virus gene start (GS) sequence and a downstream Mononegavirales virus gene end (GE) sequence, characterized in that between the GS sequence and a start codon of the foreign gene and between a stop codon of the foreign gene and the GE sequence, a 3' non-coding region- and a 5' non-coding region, genome sense, of a Mononegavirales virus gene are located, respectively, wherein the foreign gene is flanked by the 3' and 5' non-coding regions.

2. The recombinant Mononegavirales virus vector according to claim 1, characterized in that the 3' and 5' non-coding regions are of a gene encoding an envelope protein of a Mononegavirales virus selected from the group consisting of a M, G, F and HN genes.

3. The recombinant Mononegavirales virus vector according to claim 1, characterized in that the 3' and 5' non-coding regions are of a gene encoding a RNP protein of a Mononegavirales virus.

4. The recombinant Mononegavirales virus vector according to claim 1, characterized in that the foreign gene encodes an antigen of a pathogen.

5. The recombinant Mononegavirales virus vector according to claim 1, characterized in that the foreign gene encodes an immune-modulator.

6. The recombinant Mononegavirales virus vector according to claim 1, characterized in that the Mononegavirales virus vector is a virus of the family Rhabdoviridae.

7. The recombinant Mononegavirales virus vector according to claim 6, characterized in that the Mononegavirales virus vector is a rabies virus.

8. The recombinant Mononegavirales virus vector according to claim 6, characterized in that the Mononegavirales virus vector is an infectious hematopoietic necrosis virus.

9. The recombinant Mononegavirales virus vector according to claim 6, characterized in that the 3' and 5' non-coding regions are of a N, P, M or G gene.

10. The recombinant Mononegavirales virus vector according to claim 6, characterized in that the additional transcription unit is located at a 3' proximal position or between P-M, M-G or G-L genes.

11. The recombinant Mononegavirales virus vector according to claim 1, characterized in that the Mononegavirales virus vector is a virus of the family Paramyxoviridae.

12. The recombinant Mononegavirales virus vector according to claim 11, characterized in that the Mononegavirales virus vector is a Newcastle disease virus, canine distemper virus or parainfluenza virus.

13. The recombinant Mononegavirales virus vector according to claim 11, characterized in that the 3' and 5' non-coding regions are of a NP, P, M, F or HN gene.

14. The recombinant Mononegavirales virus vector according to claim 11, characterized in that the additional transcription unit is located at a 3' proximal position or between P-M, M-F, F-HN or HN-L genes.

15. The recombinant Mononegavirales virus vector according to claim 11, characterized in that the Mononegavirales virus vector is Newcastle disease virus.

16. The recombinant Mononegavirales virus vector according to claim 15, characterized in that the additional transcription unit is located between F-HN genes.

17. The recombinant Mononegavirales virus vector according to claim 15, characterized in that the non-coding regions are of a HN gene.

18. The recombinant Mononegavirales virus vector according to claim 15, characterized in that the foreign gene encodes an antigen of an avian pathogen.

19. The recombinant Mononegavirales virus vector according to claim 15, characterized in that the foreign gene encodes a hemagglutinin (HA) of an influenza virus.

20. The recombinant Mononegavirales virus vector according to claim 1, characterized in that the Mononegavirales virus vector is an attenuated virus.

21. A vaccine against a microbial pathogen, characterized in that it comprises a recombinant Mononegavirales virus vector according to claim 1 in a live or inactivated form, and a pharmaceutically acceptable carrier or diluent.

22. The vaccine according to claim 21, characterized in that it additionally comprises an adjuvant.

23. The vaccine according to claim 21, characterized in that it comprises an additional vaccine strain.

* * * * *

SEQUENCE LISTING

```
<160> NUMBER OF SEQ ID NOS: 111

<210> SEQ ID NO 1
<211> LENGTH: 133
<212> TYPE: DNA
<213> ORGANISM: Newcastle disease virus
<220> FEATURE:
<221> NAME/KEY: NDV_Fgene_end
<222> LOCATION: (1)..(11)
<220> FEATURE:
<221> NAME/KEY: NDV_F-HN_intergenic_region
<222> LOCATION: (12)..(42)
<220> FEATURE:
<221> NAME/KEY: NDV_HNgene_start
<222> LOCATION: (43)..(52)
<220> FEATURE:
<221> NAME/KEY: NDV_HNgene_5'_non_coding_region
<222> LOCATION: (53)..(133)

<400> SEQUENCE: 1
ttaagaaaaa actaccggtt gtagatgacc aaaggacgat atacgggtag aacggtaaga      60
gaggccgccc ctcaattgcg agccaggctt cacaacctcc gttctaccgc ttcaccgaca     120
acagtcctca atc                                                       133

<210> SEQ ID NO 2
<211> LENGTH: 177
<212> TYPE: DNA
<213> ORGANISM: Newcastle disease virus
<220> FEATURE:
<221> NAME/KEY: NDV_HNgene_3'_non_coding_region
<222> LOCATION: (1)..(166)
<220> FEATURE:
<221> NAME/KEY: NDV_HNgene_end
<222> LOCATION: (167)..(177)

<400> SEQUENCE: 2
```

-continued

```
ttgagtcaat tataaaggag ttggaaagat ggcattgtat cacctatctt ctgcgacatc      60
aagaatcaaa ccgaatgccg gcgcgtgctc gaattccatg ttgccagttg accacaatca     120
gccagtgctc atgcgatcag attaagcctt gtcaatagtc tcttgattaa gaaaaaa        177

<210> SEQ ID NO 3
<211> LENGTH: 133
<212> TYPE: DNA
<213> ORGANISM: Artificial
<220> FEATURE:
<223> OTHER INFORMATION: rec NDV insertion construct
<220> FEATURE:
<221> NAME/KEY: rNDV_Fgene_end
<222> LOCATION: (1)..(11)
<220> FEATURE:
<221> NAME/KEY: rNDV_F-HN_intergenic_region
<222> LOCATION: (12)..(42)
<220> FEATURE:
<221> NAME/KEY: rNDV_HNgene_start
<222> LOCATION: (43)..(52)
<220> FEATURE:
<221> NAME/KEY: rNDV_HNgene_5'_non_coding_region
<222> LOCATION: (53)..(133)

<400> SEQUENCE: 3
ttaagaaaaa actaccggtt gtagatgacc aaaggacgat atacgggtag aacggtaaga      60
gaggccgccc ctcaattgcg agccaggctt cacaacctcc gttctaccgc ttcaccgaca     120
acagtcctca acc                                                        133

<210> SEQ ID NO 4
<211> LENGTH: 177
<212> TYPE: DNA
<213> ORGANISM: Artificial
<220> FEATURE:
<223> OTHER INFORMATION: rec NDV insertion construct
<220> FEATURE:
<221> NAME/KEY: rNDV_HNgene_3'_non_coding_region
<222> LOCATION: (1)..(166)
<220> FEATURE:
<221> NAME/KEY: rNDV_HNgene_end
<222> LOCATION: (167)..(177)

<400> SEQUENCE: 4
ttgagtcaat tctaagggag ttggaaagat ggcattgtat cacctatctt ctgcgacatc      60
aagaatcaaa ccgaatgccg gcgcgtgctc gaattccatg ttgccagttg accacaatca     120
gccagtgctc atgcgatcag attaagcctt gtcaatagtc tcttgattaa gaaaaaa        177

<210> SEQ ID NO 5
<211> LENGTH: 29
<212> TYPE: DNA
<213> ORGANISM: Artificial
<220> FEATURE:
<223> OTHER INFORMATION: Cloning primer PH5F1

<400> SEQUENCE: 5
ctaaacgcgt aaaatggaga aaatagtgc                                        29

<210> SEQ ID NO 6
<211> LENGTH: 31
<212> TYPE: DNA
<213> ORGANISM: Artificial
<220> FEATURE:
<223> OTHER INFORMATION: Cloning primer PH5R1

<400> SEQUENCE: 6
tcggacgcgt ttaaatgcaa attctgcact g                                     31
```

<210> SEQ ID NO 7
<211> LENGTH: 25
<212> TYPE: DNA
<213> ORGANISM: Artificial
<220> FEATURE:
<223> OTHER INFORMATION: Cloning primer PH5F2

<400> SEQUENCE: 7
ccttccatgg agaaaatagt gcttc                                   25

<210> SEQ ID NO 8
<211> LENGTH: 54
<212> TYPE: DNA
<213> ORGANISM: Artificial
<220> FEATURE:
<223> OTHER INFORMATION: Cloning primer PH5R2

<400> SEQUENCE: 8
cctccttaag tataattgac tcaattaaat gcaaattctg cactgcaatg atcc   54

<210> SEQ ID NO 9
<211> LENGTH: 30
<212> TYPE: DNA
<213> ORGANISM: Artificial
<220> FEATURE:
<223> OTHER INFORMATION: Cloning primer MP1

<400> SEQUENCE: 9
gacaacagtc ctcaaccatg gaccgcgccg                              30

<210> SEQ ID NO 10
<211> LENGTH: 41
<212> TYPE: DNA
<213> ORGANISM: Artificial
<220> FEATURE:
<223> OTHER INFORMATION: Cloning primer MP2

<400> SEQUENCE: 10
ctggctagtt gagtcaattc ttaaggagtt ggaaagatgg c                  41

<210> SEQ ID NO 11
<211> LENGTH: 38
<212> TYPE: DNA
<213> ORGANISM: Artificial
<220> FEATURE:
<223> OTHER INFORMATION: Cloning primer MP3

<400> SEQUENCE: 11
caaaacagct catggtacgt aatacgggta ggacatgg                     38

<210> SEQ ID NO 12
<211> LENGTH: 38
<212> TYPE: DNA
<213> ORGANISM: Artificial
<220> FEATURE:
<223> OTHER INFORMATION: Cloning primer MP4

<400> SEQUENCE: 12
gtaagtggca atgcgatcgc aggcaaaaca gctcatgg                     38

<210> SEQ ID NO 13
<211> LENGTH: 43
<212> TYPE: DNA
<213> ORGANISM: Artificial
<220> FEATURE:
<223> OTHER INFORMATION: Cloning primer MP5

```
<400> SEQUENCE: 13
gaaaaaacta ccggcgatcg ctgaccaaag gacgatatac ggg                43

<210> SEQ ID NO 14
<211> LENGTH: 48
<212> TYPE: DNA
<213> ORGANISM: Artificial
<220> FEATURE:
<223> OTHER INFORMATION: Mutagenesis primer pMPMLUIGRFHNF

<400> SEQUENCE: 14
ggttgtagat gaccaaagga cgcgttacgg gtagaacggt aagagagg            48

<210> SEQ ID NO 15
<211> LENGTH: 48
<212> TYPE: DNA
<213> ORGANISM: Artificial
<220> FEATURE:
<223> OTHER INFORMATION: mutagenesis primer pMPMLUIGRFHNR

<400> SEQUENCE: 15
cctctcttac cgttctaccc gtaacgcgtc ctttggtcat ctacaacc            48

<210> SEQ ID NO 16
<211> LENGTH: 65
<212> TYPE: DNA
<213> ORGANISM: Artificial
<220> FEATURE:
<223> OTHER INFORMATION: cloning oligo OFVOF

<400> SEQUENCE: 16
aggacgcgtt acgggtagaa gattctggat cccggttggc gccctccagg tgcagcacca    60
tggag                                                               65

<210> SEQ ID NO 17
<211> LENGTH: 65
<212> TYPE: DNA
<213> ORGANISM: Artificial
<220> FEATURE:
<223> OTHER INFORMATION: cloning oligo OFVOR

<400> SEQUENCE: 17
ctccatggtg ctgcacctgg agggcgccaa ccgggatcca gaatcttcta cccgtaacgc    60
gtcct                                                               65

<210> SEQ ID NO 18
<211> LENGTH: 31
<212> TYPE: DNA
<213> ORGANISM: Artificial
<220> FEATURE:
<223> OTHER INFORMATION: cloning primer PNCRFHIF

<400> SEQUENCE: 18
atacttaagt tccctaatag taatttgtgt g                              31

<210> SEQ ID NO 19
<211> LENGTH: 58
<212> TYPE: DNA
<213> ORGANISM: Artificial
<220> FEATURE:
<223> OTHER INFORMATION: cloning primer PNCRFHIR

<400> SEQUENCE: 19
cacgcgatcg cattgccact gtacattttt tcttaactct ctgaactgac agactacc    58
```

<210> SEQ ID NO 20
<211> LENGTH: 31
<212> TYPE: DNA
<213> ORGANISM: Artificial
<220> FEATURE:
<223> OTHER INFORMATION: cloning primer BSSNH+

<400> SEQUENCE: 20
ctggtgaaaa aaactaacac ccctgctagc a                            31

<210> SEQ ID NO 21
<211> LENGTH: 39
<212> TYPE: DNA
<213> ORGANISM: Artificial
<220> FEATURE:
<223> OTHER INFORMATION: cloning primer BSSNH-

<400> SEQUENCE: 21
cgttgaccac ttttttttgat tgtggggacg atcgttcga                   39

<210> SEQ ID NO 22
<211> LENGTH: 50
<212> TYPE: DNA
<213> ORGANISM: Artificial
<220> FEATURE:
<223> OTHER INFORMATION: cloning primer RABGNCRoligo1

<400> SEQUENCE: 22
ctggtgaaaa aaactattaa catccctcaa aagactcaag gatacgtact        50

<210> SEQ ID NO 23
<211> LENGTH: 49
<212> TYPE: DNA
<213> ORGANISM: Artificial
<220> FEATURE:
<223> OTHER INFORMATION: cloning primer RABGNCRoligo2

<400> SEQUENCE: 23
gtatccttga gtcttttgag ggatgttaat agttttttc accagttgc          49

<210> SEQ ID NO 24
<211> LENGTH: 50
<212> TYPE: DNA
<213> ORGANISM: Artificial
<220> FEATURE:
<223> OTHER INFORMATION: cloning primer RABGNCRoligo3

<400> SEQUENCE: 24
ggccgtcctt tcaacgatcc aagtcctgaa gatcacctcc ccttggggga        50

<210> SEQ ID NO 25
<211> LENGTH: 59
<212> TYPE: DNA
<213> ORGANISM: Artificial
<220> FEATURE:
<223> OTHER INFORMATION: cloning primer RABGNCRoligo4

<400> SEQUENCE: 25
agcttccccc aaggggaggt gatcttcagg acttggatcg ttgaaaggac ggccagtac    59

<210> SEQ ID NO 26
<211> LENGTH: 20
<212> TYPE: DNA
<213> ORGANISM: Artificial
<220> FEATURE:
<223> OTHER INFORMATION: cloning primer EIAsynCDF -continued

```
<400> SEQUENCE: 26
atggtgtcca tcgccttcta                                        20

<210> SEQ ID NO 27
<211> LENGTH: 21
<212> TYPE: DNA
<213> ORGANISM: Artificial
<220> FEATURE:
<223> OTHER INFORMATION: cloning primer EIAsynCDstopR

<400> SEQUENCE: 27
tcagtgtatg ttgtgttggg c                                      21

<210> SEQ ID NO 28
<211> LENGTH: 24
<212> TYPE: DNA
<213> ORGANISM: respiratory syncytial virus

<400> SEQUENCE: 28
cattagatca gaagaacaac tggc                                   24

<210> SEQ ID NO 29
<211> LENGTH: 13
<212> TYPE: DNA
<213> ORGANISM: Infectious hematopoietic necrosis virus

<400> SEQUENCE: 29
ggcacttcag ttg                                               13

<210> SEQ ID NO 30
<211> LENGTH: 10
<212> TYPE: DNA
<213> ORGANISM: Infectious hematopoietic necrosis virus

<400> SEQUENCE: 30
tagaaaaaaa                                                   10

<210> SEQ ID NO 31
<211> LENGTH: 13
<212> TYPE: DNA
<213> ORGANISM: Infectious hematopoietic necrosis virus

<400> SEQUENCE: 31
ggcactatag tgc                                               13

<210> SEQ ID NO 32
<211> LENGTH: 13
<212> TYPE: DNA
<213> ORGANISM: Infectious hematopoietic necrosis virus

<400> SEQUENCE: 32
ggcacgcaag tgt                                               13

<210> SEQ ID NO 33
<211> LENGTH: 13
<212> TYPE: DNA
<213> ORGANISM: Infectious hematopoietic necrosis virus

<400> SEQUENCE: 33
agacagaaaa aaa                                               13

<210> SEQ ID NO 34
<211> LENGTH: 13
```

```
<212> TYPE: DNA
<213> ORGANISM: Infectious hematopoietic necrosis virus

<400> SEQUENCE: 34
ggcacttttg tgc                                                          13

<210> SEQ ID NO 35
<211> LENGTH: 13
<212> TYPE: DNA
<213> ORGANISM: Infectious hematopoietic necrosis virus

<400> SEQUENCE: 35
ggcacatttg tgc                                                          13

<210> SEQ ID NO 36
<211> LENGTH: 13
<212> TYPE: DNA
<213> ORGANISM: Infectious hematopoietic necrosis virus

<400> SEQUENCE: 36
agatagaaaa aaa                                                          13

<210> SEQ ID NO 37
<211> LENGTH: 13
<212> TYPE: DNA
<213> ORGANISM: Infectious hematopoietic necrosis virus

<400> SEQUENCE: 37
agatacaaaa aaa                                                          13

<210> SEQ ID NO 38
<211> LENGTH: 10
<212> TYPE: DNA
<213> ORGANISM: Sendai virus

<400> SEQUENCE: 38
agggtcaaag                                                              10

<210> SEQ ID NO 39
<211> LENGTH: 10
<212> TYPE: DNA
<213> ORGANISM: Sendai virus

<400> SEQUENCE: 39
agggtgaaag                                                              10

<210> SEQ ID NO 40
<211> LENGTH: 10
<212> TYPE: DNA
<213> ORGANISM: Sendai virus

<400> SEQUENCE: 40
agggataaag                                                              10

<210> SEQ ID NO 41
<211> LENGTH: 10
<212> TYPE: DNA
<213> ORGANISM: Sendai virus

<400> SEQUENCE: 41
agggtgaatg                                                              10

<210> SEQ ID NO 42
<211> LENGTH: 12
```

```
<212> TYPE: DNA
<213> ORGANISM: Human parainfluenza virus 2

<400> SEQUENCE: 42
aagtaagaaa aa                                                         12

<210> SEQ ID NO 43
<211> LENGTH: 10
<212> TYPE: DNA
<213> ORGANISM: Human parainfluenza virus 2

<400> SEQUENCE: 43
agggtgaatg                                                            10

<210> SEQ ID NO 44
<211> LENGTH: 12
<212> TYPE: DNA
<213> ORGANISM: Human parainfluenza virus 2

<400> SEQUENCE: 44
aattaagaaa aa                                                         12

<210> SEQ ID NO 45
<211> LENGTH: 12
<212> TYPE: DNA
<213> ORGANISM: Human parainfluenza virus 2

<400> SEQUENCE: 45
aaataagaaa aa                                                         12

<210> SEQ ID NO 46
<211> LENGTH: 10
<212> TYPE: DNA
<213> ORGANISM: Human parainfluenza virus 2

<400> SEQUENCE: 46
agggacaaag                                                            10

<210> SEQ ID NO 47
<211> LENGTH: 10
<212> TYPE: DNA
<213> ORGANISM: Human parainfluenza virus 2

<400> SEQUENCE: 47
agggttaaag                                                            10

<210> SEQ ID NO 48
<211> LENGTH: 12
<212> TYPE: DNA
<213> ORGANISM: Human parainfluenza virus 2

<400> SEQUENCE: 48
gaataagaaa aa                                                         12

<210> SEQ ID NO 49
<211> LENGTH: 10
<212> TYPE: DNA
<213> ORGANISM: Human parainfluenza virus 2

<400> SEQUENCE: 49
agggttaatg                                                            10

<210> SEQ ID NO 50
<211> LENGTH: 12
```

```
<212> TYPE: DNA
<213> ORGANISM: Human parainfluenza virus 2

<400> SEQUENCE: 50
tagtaagaaa aa                                                        12

<210> SEQ ID NO 51
<211> LENGTH: 10
<212> TYPE: DNA
<213> ORGANISM: Bovine parainfluenza virus 3

<400> SEQUENCE: 51
aggattaaag                                                           10

<210> SEQ ID NO 52
<211> LENGTH: 10
<212> TYPE: DNA
<213> ORGANISM: Bovine parainfluenza virus 3

<400> SEQUENCE: 52
aggatgaaag                                                           10

<210> SEQ ID NO 53
<211> LENGTH: 10
<212> TYPE: DNA
<213> ORGANISM: Bovine parainfluenza virus 3

<400> SEQUENCE: 53
aggatcaaag                                                           10

<210> SEQ ID NO 54
<211> LENGTH: 10
<212> TYPE: DNA
<213> ORGANISM: Bovine parainfluenza virus 3

<400> SEQUENCE: 54
aggaacaaag                                                           10

<210> SEQ ID NO 55
<211> LENGTH: 10
<212> TYPE: DNA
<213> ORGANISM: Bovine parainfluenza virus 3

<400> SEQUENCE: 55
taataaaaaa                                                           10

<210> SEQ ID NO 56
<211> LENGTH: 10
<212> TYPE: DNA
<213> ORGANISM: Bovine parainfluenza virus 3

<400> SEQUENCE: 56
aggagaaaag                                                           10

<210> SEQ ID NO 57
<211> LENGTH: 10
<212> TYPE: DNA
<213> ORGANISM: Human parainfluenza virus 3

<400> SEQUENCE: 57
taatcaaaaa                                                           10

<210> SEQ ID NO 58
<211> LENGTH: 10
```

-continued

<212> TYPE: DNA
<213> ORGANISM: Human parainfluenza virus 3

<400> SEQUENCE: 58
aggacaaaag 10

<210> SEQ ID NO 59
<211> LENGTH: 10
<212> TYPE: DNA
<213> ORGANISM: Human parainfluenza virus 3

<400> SEQUENCE: 59
aggacaaaag 10

<210> SEQ ID NO 60
<211> LENGTH: 10
<212> TYPE: DNA
<213> ORGANISM: Human parainfluenza virus 3

<400> SEQUENCE: 60
aggagtaaag 10

<210> SEQ ID NO 61
<211> LENGTH: 10
<212> TYPE: DNA
<213> ORGANISM: Human parainfluenza virus 3

<400> SEQUENCE: 61
aggagcaaag 10

<210> SEQ ID NO 62
<211> LENGTH: 11
<212> TYPE: DNA
<213> ORGANISM: Measles virus

<400> SEQUENCE: 62
aggattcaaa g 11

<210> SEQ ID NO 63
<211> LENGTH: 10
<212> TYPE: DNA
<213> ORGANISM: Measles virus

<400> SEQUENCE: 63
aggaaccagg 10

<210> SEQ ID NO 64
<211> LENGTH: 10
<212> TYPE: DNA
<213> ORGANISM: Measles virus

<400> SEQUENCE: 64
agggccaagg 10

<210> SEQ ID NO 65
<211> LENGTH: 10
<212> TYPE: DNA
<213> ORGANISM: Measles virus

<400> SEQUENCE: 65
agggtgcaag 10

<210> SEQ ID NO 66
<211> LENGTH: 10

```
<212> TYPE: DNA
<213> ORGANISM: Measles virus

<400> SEQUENCE: 66
ttaagaaaaa                                                          10

<210> SEQ ID NO 67
<211> LENGTH: 10
<212> TYPE: DNA
<213> ORGANISM: Measles virus

<400> SEQUENCE: 67
agggtccaag                                                          10

<210> SEQ ID NO 68
<211> LENGTH: 10
<212> TYPE: DNA
<213> ORGANISM: Measles virus

<400> SEQUENCE: 68
ttaaagaaaa                                                          10

<210> SEQ ID NO 69
<211> LENGTH: 10
<212> TYPE: DNA
<213> ORGANISM: Rinderpest virus

<400> SEQUENCE: 69
aggattcaag                                                          10

<210> SEQ ID NO 70
<211> LENGTH: 10
<212> TYPE: DNA
<213> ORGANISM: Rinderpest virus

<400> SEQUENCE: 70
aggacccagg                                                          10

<210> SEQ ID NO 71
<211> LENGTH: 10
<212> TYPE: DNA
<213> ORGANISM: Rinderpest virus

<400> SEQUENCE: 71
aggagcaaag                                                          10

<210> SEQ ID NO 72
<211> LENGTH: 12
<212> TYPE: DNA
<213> ORGANISM: Rinderpest virus

<400> SEQUENCE: 72
taccaaacaa aa                                                       12

<210> SEQ ID NO 73
<211> LENGTH: 12
<212> TYPE: DNA
<213> ORGANISM: Rinderpest virus

<400> SEQUENCE: 73
tataaacaaa aa                                                       12

<210> SEQ ID NO 74
<211> LENGTH: 10
```

```
<212> TYPE: DNA
<213> ORGANISM: Rinderpest virus

<400> SEQUENCE: 74
aggatgcaag                                                          10

<210> SEQ ID NO 75
<211> LENGTH: 10
<212> TYPE: DNA
<213> ORGANISM: canine distemper virus

<400> SEQUENCE: 75
agggtcaatg                                                          10

<210> SEQ ID NO 76
<211> LENGTH: 10
<212> TYPE: DNA
<213> ORGANISM: canine distemper virus

<400> SEQUENCE: 76
aggacccagg                                                          10

<210> SEQ ID NO 77
<211> LENGTH: 10
<212> TYPE: DNA
<213> ORGANISM: canine distemper virus

<400> SEQUENCE: 77
aggacacaag                                                          10

<210> SEQ ID NO 78
<211> LENGTH: 13
<212> TYPE: DNA
<213> ORGANISM: canine distemper virus

<400> SEQUENCE: 78
taattaatca aaa                                                      13

<210> SEQ ID NO 79
<211> LENGTH: 10
<212> TYPE: DNA
<213> ORGANISM: canine distemper virus

<400> SEQUENCE: 79
agggtccagg                                                          10

<210> SEQ ID NO 80
<211> LENGTH: 10
<212> TYPE: DNA
<213> ORGANISM: canine distemper virus

<400> SEQUENCE: 80
ttaaagaaaa                                                          10

<210> SEQ ID NO 81
<211> LENGTH: 10
<212> TYPE: DNA
<213> ORGANISM: canine distemper virus

<400> SEQUENCE: 81
agggctcagg                                                          10

<210> SEQ ID NO 82
<211> LENGTH: 11
```

```
<212> TYPE: DNA
<213> ORGANISM: canine distemper virus

<400> SEQUENCE: 82
ttataaaaaa a                                                              11

<210> SEQ ID NO 83
<211> LENGTH: 10
<212> TYPE: DNA
<213> ORGANISM: canine distemper virus

<400> SEQUENCE: 83
aggatccaag                                                                10

<210> SEQ ID NO 84
<211> LENGTH: 12
<212> TYPE: DNA
<213> ORGANISM: canine distemper virus

<400> SEQUENCE: 84
tacgaaaaaa aa                                                             12

<210> SEQ ID NO 85
<211> LENGTH: 13
<212> TYPE: DNA
<213> ORGANISM: Simian virus 5

<400> SEQUENCE: 85
aggtccggaa cct                                                            13

<210> SEQ ID NO 86
<211> LENGTH: 14
<212> TYPE: DNA
<213> ORGANISM: Simian virus 5

<400> SEQUENCE: 86
tttaaagaaa aaaa                                                           14

<210> SEQ ID NO 87
<211> LENGTH: 14
<212> TYPE: DNA
<213> ORGANISM: Simian virus 5

<400> SEQUENCE: 87
aggcccggac gggt                                                           14

<210> SEQ ID NO 88
<211> LENGTH: 12
<212> TYPE: DNA
<213> ORGANISM: Simian virus 5

<400> SEQUENCE: 88
ttttagaaaa aa                                                             12

<210> SEQ ID NO 89
<211> LENGTH: 16
<212> TYPE: DNA
<213> ORGANISM: Simian virus 5

<400> SEQUENCE: 89
cgattaacga taaata                                                         16

<210> SEQ ID NO 90
<211> LENGTH: 12
```

```
<212> TYPE: DNA
<213> ORGANISM: Simian virus 5

<400> SEQUENCE: 90
agcccgaaca ct                                                     12

<210> SEQ ID NO 91
<211> LENGTH: 11
<212> TYPE: DNA
<213> ORGANISM: Simian virus 5

<400> SEQUENCE: 91
ttcaaagaaa a                                                      11

<210> SEQ ID NO 92
<211> LENGTH: 22
<212> TYPE: DNA
<213> ORGANISM: Simian virus 5

<400> SEQUENCE: 92
caatcatatt aagactatcc ta                                          22

<210> SEQ ID NO 93
<211> LENGTH: 13
<212> TYPE: DNA
<213> ORGANISM: Simian virus 5

<400> SEQUENCE: 93
agcacgaacc cat                                                    13

<210> SEQ ID NO 94
<211> LENGTH: 15
<212> TYPE: DNA
<213> ORGANISM: Simian virus 5

<400> SEQUENCE: 94
tttttaagaa aaaaa                                                  15

<210> SEQ ID NO 95
<211> LENGTH: 12
<212> TYPE: DNA
<213> ORGANISM: Simian virus 5

<400> SEQUENCE: 95
aggaccgaac ct                                                     12

<210> SEQ ID NO 96
<211> LENGTH: 14
<212> TYPE: DNA
<213> ORGANISM: Simian virus 5

<400> SEQUENCE: 96
ttttaaagaa aaaa                                                   14

<210> SEQ ID NO 97
<211> LENGTH: 13
<212> TYPE: DNA
<213> ORGANISM: Simian virus 5

<400> SEQUENCE: 97
aggcccgaac act                                                    13

<210> SEQ ID NO 98
<211> LENGTH: 12
```

```
<212> TYPE: DNA
<213> ORGANISM: Simian virus 5

<400> SEQUENCE: 98
ttttaagaaa aa                                                         12

<210> SEQ ID NO 99
<211> LENGTH: 13
<212> TYPE: DNA
<213> ORGANISM: Simian virus 5

<400> SEQUENCE: 99
ccaagagaac aat                                                        13

<210> SEQ ID NO 100
<211> LENGTH: 11
<212> TYPE: DNA
<213> ORGANISM: Simian virus 5

<400> SEQUENCE: 100
aggccagaat g                                                          11

<210> SEQ ID NO 101
<211> LENGTH: 12
<212> TYPE: DNA
<213> ORGANISM: Simian virus 5

<400> SEQUENCE: 101
tttaagaaaa aa                                                         12

<210> SEQ ID NO 102
<211> LENGTH: 10
<212> TYPE: DNA
<213> ORGANISM: Vesicular stomatitis virus

<400> SEQUENCE: 102
aacagtaatc                                                            10

<210> SEQ ID NO 103
<211> LENGTH: 10
<212> TYPE: DNA
<213> ORGANISM: Vesicular stomatitis virus

<400> SEQUENCE: 103
aacagatatc                                                            10

<210> SEQ ID NO 104
<211> LENGTH: 10
<212> TYPE: DNA
<213> ORGANISM: Vesicular stomatitis virus

<400> SEQUENCE: 104
aacagagatc                                                            10

<210> SEQ ID NO 105
<211> LENGTH: 10
<212> TYPE: DNA
<213> ORGANISM: Vesicular stomatitis virus

<400> SEQUENCE: 105
aacagcaatc                                                            10

<210> SEQ ID NO 106
<211> LENGTH: 10
```

```
<212> TYPE: DNA
<213> ORGANISM: Newcastle disease virus

<400> SEQUENCE: 106
acgggtagaa                                                              10

<210> SEQ ID NO 107
<211> LENGTH: 10
<212> TYPE: DNA
<213> ORGANISM: Newcastle disease virus

<400> SEQUENCE: 107
ttagaaaaaa                                                              10

<210> SEQ ID NO 108
<211> LENGTH: 11
<212> TYPE: DNA
<213> ORGANISM: Newcastle disease virus

<400> SEQUENCE: 108
ttaagaaaaa a                                                            11

<210> SEQ ID NO 109
<211> LENGTH: 31
<212> TYPE: DNA
<213> ORGANISM: Newcastle disease virus

<400> SEQUENCE: 109
ctaccggttg tagatgacca aaggacgata t                                      31

<210> SEQ ID NO 110
<211> LENGTH: 47
<212> TYPE: DNA
<213> ORGANISM: Newcastle disease virus

<400> SEQUENCE: 110
tgtaagtggc aatgagatac aaggcaaaac agctcatggt aaataat                     47

<210> SEQ ID NO 111
<211> LENGTH: 10
<212> TYPE: DNA
<213> ORGANISM: Newcastle disease virus

<400> SEQUENCE: 111
acgggtagga                                                              10
```